(12) United States Patent
Chen et al.

(10) Patent No.: US 12,420,112 B2
(45) Date of Patent: Sep. 23, 2025

(54) AUTOMATIC BEAM MODELING BASED ON DEEP LEARNING

(71) Applicant: Elekta (Shanghai) Technology Co., Ltd., Shanghai (CN)

(72) Inventors: Shufei Chen, Shanghai (CN); Lu Yuan, Shanghai (CN)

(73) Assignee: Elekta (Shanghai) Technology Co., Ltd., Shanghai (CN)

( * ) Notice: Subject to any disclaimer, the term of this patent is extended or adjusted under 35 U.S.C. 154(b) by 277 days.

(21) Appl. No.: 18/043,755

(22) PCT Filed: Sep. 2, 2020

(86) PCT No.: PCT/CN2020/112920
§ 371 (c)(1),
(2) Date: Mar. 2, 2023

(87) PCT Pub. No.: WO2022/047637
PCT Pub. Date: Mar. 10, 2022

(65) Prior Publication Data
US 2023/0285774 A1 Sep. 14, 2023

(51) Int. Cl.
*A61N 5/10* (2006.01)
*G16H 20/40* (2018.01)
(52) U.S. Cl.
CPC .......... *A61N 5/1031* (2013.01); *G16H 20/40* (2018.01); *A61N 2005/1035* (2013.01); *A61N 2005/1089* (2013.01)
(58) Field of Classification Search
CPC .......... A61N 5/1031; A61N 2005/1035; A61N 2005/1089; A61N 2005/1041;
(Continued)

(56) References Cited

U.S. PATENT DOCUMENTS

2015/0094519 A1  4/2015  Kuusela et al.
2019/0175952 A1  6/2019  Hissoiny
(Continued)

FOREIGN PATENT DOCUMENTS

CN  108415058  8/2018
CN  109843377  6/2019
(Continued)

OTHER PUBLICATIONS

"International Application Serial No. PCT/CN2020/112920, International Search Report mailed May 26, 2021", 5 pgs.
(Continued)

*Primary Examiner* — Kiho Kim
(74) *Attorney, Agent, or Firm* — Schwegman Lundberg & Woessner, P.A.

(57) ABSTRACT

Systems and methods for generating a beam model for radiotherapy treatment planning are discussed. An exemplary system includes a memory to store a trained deep learning model, and a processor circuit to generate a beam model. The deep learning model can be trained to establish a relationship between machine scanning data and values of beam model parameters, and validated for accuracy. The processor circuit can receive machine scanning data indicative of a configuration or an operation status of the radiation therapy device, apply the machine scanning data to the trained deep learning model to determine values for the beam model parameters, and generate a beam model based on the determined values of the plurality of beam model parameters. The beam model may be provided to a user, or a treatment planning system.

22 Claims, 13 Drawing Sheets

(58) Field of Classification Search
CPC .......... A61N 2005/1055; A61N 5/103; G16H 20/40; G06N 3/0442; G06N 3/0464; G06N 3/0475; G06N 3/084; G06N 7/01; G06N 20/00; G06N 3/09

See application file for complete search history.

(56) References Cited

U.S. PATENT DOCUMENTS

| | | |
|---|---|---|
| 2019/0192880 A1 | 6/2019 | Hibbard |
| 2019/0333623 A1 | 10/2019 | Hibbard |
| 2020/0075148 A1* | 3/2020 | Nguyen .................. G16H 20/10 |

FOREIGN PATENT DOCUMENTS

| | | |
|---|---|---|
| CN | 110290832 | 9/2019 |
| CN | 110944717 | 3/2020 |
| CN | 111432879 | 7/2020 |
| CN | 108717866 | 10/2022 |
| CN | 116096461 | 9/2024 |
| WO | WO-2014187866 A1 | 11/2014 |
| WO | 2019113234 | 6/2019 |
| WO | WO-2022047637 A1 | 3/2022 |

OTHER PUBLICATIONS

"International Application Serial No. PCT/CN2020/112920, Written Opinion mailed May 26, 2021", 4 pgs.
"European Application Serial No. 20951885.1, Response to Communication Pursuant to Rules 161 and 162 EPC filed Aug. 31, 2023", 4 pgs.
"European Application Serial No. 20951885.1, Extended European Search Report mailed Mar. 12, 2024", 8 pgs.
"Chinese Application Serial No. 202080103747.3, Office Action mailed Apr. 22, 2024", W English Translation, 20 pgs.
"Chinese Application Serial No. 202080103747.3, Response filed Jun. 21, 2024 to Office Action mailed Apr. 22, 2024", w current English claims, 15 pgs.
"European Application Serial No. 20951885.1, Response filed Sep. 26, 2024 to Extended European Search Report mailed Mar. 12, 2024", 10 pgs.

* cited by examiner

AUTOMATIC BEAM MODELING BASED ON DEEP LEARNING

PRIORITY APPLICATIONS

This application is a U.S. National Stage Filing under 35 U.S.C. § 371 from International Application No. PCT/CN2020/112920, filed on Sep. 2, 2020, and published as WO2022/047637 on Mar. 10, 2022; the benefit of priority of which is hereby claimed herein, and which application and publication are hereby incorporated herein by reference in its entirety.

TECHNICAL FIELD

This document relates generally to dose calculation in a radiation therapy treatment system, and more particularly, to systems and methods for automatically generating a beam model for use in radiotherapy treatment planning.

BACKGROUND

Radiation therapy (or "radiotherapy") can be used to treat cancers or other ailments in mammalian (e.g., human and animal) tissue. One such radiotherapy technique is provided using a linear accelerator (also referred to as "linac"), whereby a tumor is irradiated by high-energy X-rays or electrons. The goal of radiation therapy is to maximize radiation dose to target tissue (e.g., tumor or other abnormal tissue) while minimizing damage to the surrounding healthy tissue. A physician prescribes a predefined amount of radiation dose to the target (tumor or other abnormal tissue) and clinical dose constraints for surrounding organs similar to a prescription for medicine. Generally, ionizing radiation in the form of a collimated beam is directed from an external radiation source toward a patient. The radiation beam can be accurately controlled to ensure the dose delivery.

A specified or selectable beam energy can be used for delivering a diagnostic energy level range or a therapeutic energy level range. Modulation of a radiation beam may be provided by one or more attenuators or collimators, such as a multi-leaf collimator (MLC) and jaws. The intensity and shape of the radiation beam can be adjusted by collimators to avoid damaging healthy tissue adjacent to the targeted tissue, such as by conforming the projected beam to a profile of the targeted tissue.

Treatment planning is a process involving determination of specific radiotherapy parameters for implementing a treatment goal under the constraints. Examples of the radiotherapy parameters include radiation beam angles, dose intensity level, dose distribution, etc. The radiation dose can be calculated using a dose calculation algorithm. The outcome of the treatment planning process is a radiotherapy treatment plan (also referred to as a "treatment plan" or simply a "plan"). The treatment plan can be developed using a treatment planning system (TPS). A treatment plan is custom designed for each patient before radiotherapy delivery can be delivered to a patient. In order to create a plan, one or more medical imaging techniques, such as images from X-rays, computed tomography (CT), nuclear magnetic resonance (MR), positron emission tomography (PET), single-photon emission computed tomography (SPECT), or ultrasound may be used to provide images of a target tumor. A clinician may use images of patient anatomy to identify target tumors and surrounding organs near the tumor, delineate the target that is to receive a prescribed radiation dose, and similarly delineate nearby tissue such as organs at risk (OARs) that may be damaged from the radiation treatment. The delineation, or the contouring of the target tumor from the OARs, can be done manually, or by using an automated software tool that assists in identifying or delineating the target tumor and OARs. A radiation therapy treatment plan can then be generated using an optimization technique based on clinical and dosimetric objectives and constraints (e.g., the maximum, minimum, mean, and a fraction of dose to a fraction or the whole tumor volume, and similar measures for the critical organs).

The dose distribution of the treatment plan can be generated using a dose calculation algorithm. A beam model for the algorithm includes parameters that describe energy distribution of radiation emitted from the radiation therapy machine (e.g., a linac). The beam model parameter values can vary from one radiation therapy machine to another, even radiation therapy machines of the same model from the same manufacturer require different beam model parameters. Mechanical differences (e.g., mechanical dimensions or material properties) or differences in component values (e.g., electronic circuit component values) can contribute to the differences in beam model parameter values between different radiation therapy machines. A medical physicist can perform beam modeling by adjusting the model parameters manually to closely match the beam model output dose distribution with the measurements from the machine.

OVERVIEW

Treatment planning is a process of determining radiotherapy parameters for use to treat a patient via a radiation therapy device. The treatment planning procedure may include using a three-dimensional (3D) image of the patient to identify a target region (e.g., the tumor) and to identify critical organs near the tumor. Creation of a treatment plan can be a time-consuming process where a planner tries to comply with various treatment objectives or constraints (e.g., dose-volume histogram (DVH), overlap volume histogram (OVH)), taking into account their individual importance (e.g., weighting) in order to produce a treatment plan that is clinically acceptable. The treatment plan is comprised of numerical parameters that specify the direction, cross-sectional shape, and intensity of one or more radiation beams. Once generated, the treatment plan can be executed by positioning the patient in the treatment machine and delivering the prescribed radiation therapy directed by the optimized plan parameters. In some examples, the radiation therapy treatment plan may include dose "fractioning," whereby a sequence of radiation treatments may be provided to the patient over a predetermined period of time (e.g., 30-45 fractions may occur during a treatment of a patient), with each treatment including a specified fraction of a total prescribed dose. During treatment, the position of the patient and the position of the target tumor in relation to the treatment machine (e.g., linac) are important considerations to ensure the target tumor and not healthy tissue is irradiated.

For a treatment planning system (TPS), to use a dose calculation algorithm to compute dose for a specific linac requires a beam model of the dose algorithm created for the linac. The generation of beam model is part of a TPS commissioning. A beam model may include parameters that describe, among other things, the energy distribution of radiation emitted from the radiation therapy machine which is a critical input for TPS to compute dose distributions. In certain approaches, after the radiation therapy machine is installed and final tuning is performed, a customer can perform measurements of the radiation beam at different settings using a phantom (e.g., a water phantom) for beam modeling references.

An important aspect of treatment planning and beam modeling is determining beam model parameter values. Conventional beam modeling often requires a human modeler (e.g., a modeling physicist) to manually tune the beam model parameters, and apply the beam model that has the manually tuned model parameters to a dose engine to calculate a dose metric (e.g., a dose distribution or a dose profile). In virtual phantom. A human expert (e.g., the same human modeler, or a different person such as a radiation oncologist or a medical physicist) can verify that the calculated dose satisfies a pre-determined dosimetric verification criterion. The dosimetric verification criterion can be based on the analysis of a limited number of points in low-dose gradient areas, or the measurement of distances between isodose lines in high-dose gradient areas. The human expert can compare the desired dose and measurement results by placing a detector (e.g., ionization chamber) in phantom (e.g., water phantom) to visualize their discrepancy, and to check any differences or to verify consistency. If the calculated dose does not satisfy the pre-determined dosimetric verification criterion, further manual tuning of the beam model parameters may be performed until the calculated dose metric based on the beam model satisfies the pre-determined dosimetric verification criterion.

Manual tuning of beam model parameters and generating a corresponding beam model can be time-consuming and inefficient. In some instances, a human modeler is tasked with generating separate beam models such as for different energy levels (e.g., 6, 10, or 15 MV), and/or for different types of collimators. The manual tuning and testing of beam model parameters may take a long time to complete as well as a high demand of effort. Additionally, in some instances, manual tuning can be inconsistent and lead to interpretation errors, particularly for dose plans for more advanced radiation therapy techniques (e.g., intensity-modulated radiation therapy (IMRT) or volumetric-modulated arc therapy (VMAT)) that involve more complicated dose metrics and distribution representations and more complex dose calculations. For example, the integrity and complexity of the IMRT dose delivery technique relies on quantification of the coincidence of the planned and delivered IMRT dose distributions. As such, manual beam modeling and parameter tuning can be especially time-consuming and burdensome.

The present document discusses systems, devices, and methods for generating a beam model using an artificial intelligence (AI)-based approach. An exemplary system includes a memory to store a trained deep learning model, and a processor circuit to generate a beam model. The deep learning model can be trained to establish a relationship between machine scanning data and values of beam model parameters, and validated for accuracy. The processor circuit can receive machine scanning data indicative of a configuration or an operation status of the radiation therapy device, apply the machine scanning data to the trained deep learning model to determine values for the beam model parameters, and generate a beam model based on the determined values of the plurality of beam model parameters. The beam model may be provided to a user, or a treatment planning system.

The AI-based beam modeling in accordance with various examples discussed in this document may improve the efficiency and quality of beam modeling in advanced radiation therapy. Compared to conventional manual modeling approaches, the automatic beam modeling based on deep learning (DL) as discussed herein can reduce the model development and deployment cycle, reduce workload of human modelers, improve model accuracy and treatment planning efficiency. In contrast to manual dose modeling which requires a large amount of dose calculations for each manually tuned value of the model parameter, with the AI-based beam modeling as discussed in accordance with various examples herein, the dose distribution may be calculated only once to determine whether the beam model satisfies delivery criteria. As a result, overall cost savings for beam modeling and treatment planning, and improved radiotherapy, can be achieved.

The above is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various examples discussed in the present document.

DETAILED DESCRIPTION

In the following detailed description, reference is made to the accompanying drawings which form a part hereof, and which is shown by way of illustration-specific examples in which the present disclosure may be practiced. These examples, which are also referred to herein as "examples," are described in sufficient detail to enable those skilled in the art to practice the disclosure, and it is to be understood that the examples may be combined, or that other examples may be utilized and that structural, logical and electrical changes may be made without departing from the scope of the present disclosure. The following detailed description is, therefore, not be taken in a limiting sense, and the scope of the present disclosure is defined by the appended aspects and their equivalents.

Figure 1:
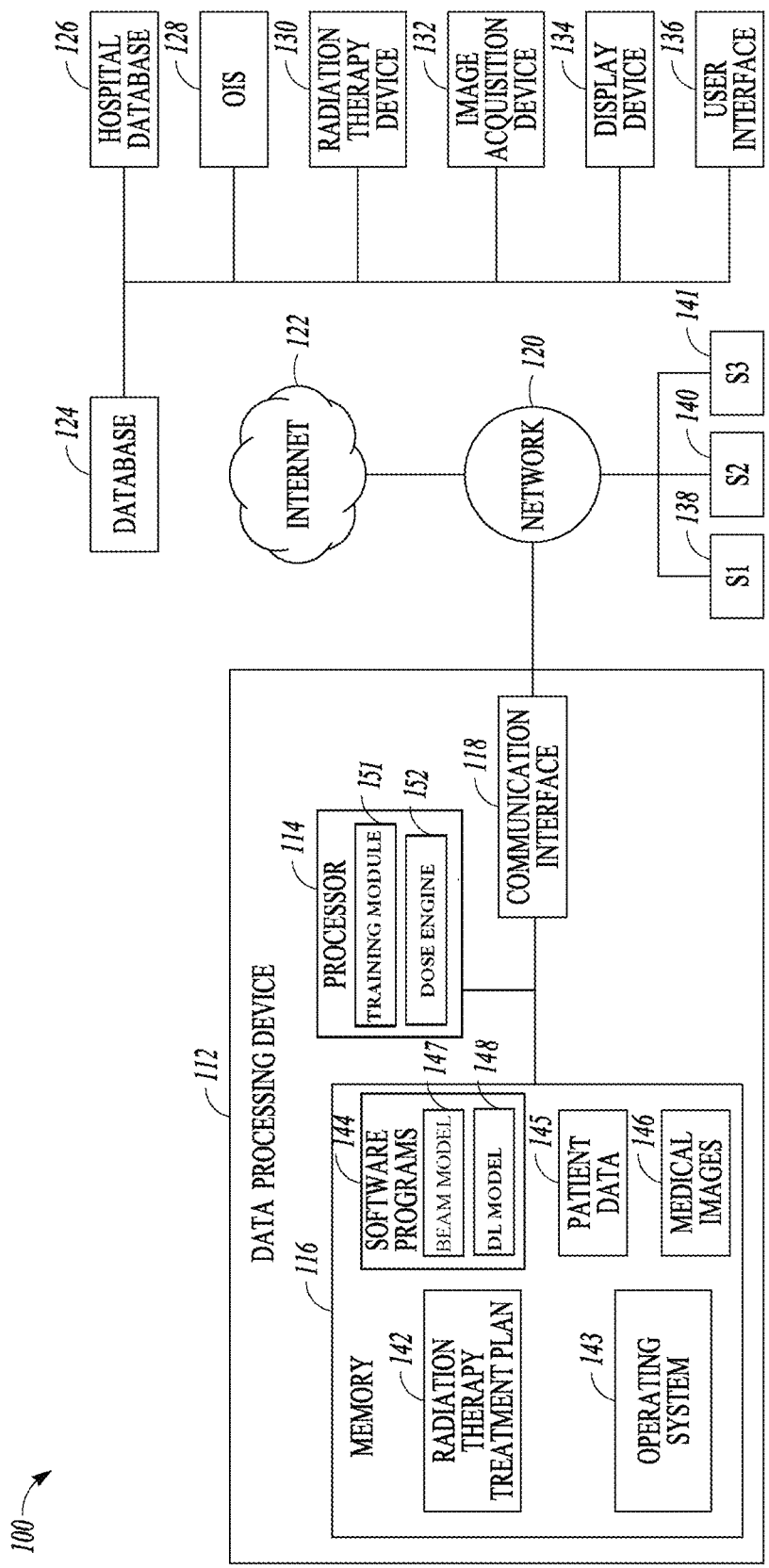
FIG. 1 illustrates an exemplary radiotherapy system.

FIG. 1 illustrates an exemplary radiotherapy system 100 for providing radiation therapy to a patient. The radiotherapy system 100 includes, among other components, a data processing device 112. The data processing device 112 may be connected to a network 120. The network 120 may be connected to the Internet 122. The network 120 can connect the data processing device 112 with one or more of a database 124, a hospital database 126, an oncology information system (OIS) 128, a radiation therapy device 130, an image acquisition device 132, a display device 134, and a user interface 136. The data processing device 112 can be configured to generate radiation therapy treatment plans 142 to be used by the radiation therapy device 130.

The data processing device 112 may include a memory 116, a processor 114, and a communication interface 118. The memory 116 may store computer-executable instructions, such as a radiation therapy treatment plan 142 (e.g., original treatment plans, adapted treatment plans and the like), an operating system 143, software programs 144, and any other computer-executable instructions to be executed by the processor 114. The memory 116 may additionally store data, such as medical images 146, patient data 145, and other data required to implement a radiation therapy treatment plan 142.

The software programs 144 may include one or more software packages that, when executed by a machine such as the processor 114, can perform specific image processing and generating a radiation treatment plan 142. In an example, the software programs 144 can convert medical images of one format (e.g., MRI) to another format (e.g., CT) by producing synthetic images, such as pseudo-CT images. For instance, the software programs 144 may include image processing programs to train a predictive model for converting a medical image from the medical images 146 in one modality (e.g., an MR image) into a synthetic image of a different modality (e.g., a pseudo CT image); alternatively, the trained predictive model may convert a CT image into an MR image. In another example, the software programs 144 may register the patient image (e.g., a CT image or an MR image) with that patient's dose distribution (also represented as an image) so that corresponding image voxels and dose voxels are associated appropriately by the network. In yet another example, the software programs 144 may substitute functions of the patient images such as signed distance functions or processed versions of the images that emphasize some aspect of the image information. Such functions might emphasize edges or differences in voxel textures, or any other structural aspect useful to neural network learning. The software programs 144 may substitute functions of the dose distribution that emphasize some aspect of the dose information. Such functions might emphasize steep gradients around the target or any other structural aspect useful to neural network learning.

In an example, the software programs 144 may generate projection images for a set of two-dimensional (2D) and/or 3D CT or MR images depicting an anatomy (e.g., one or more targets and one or more OARs) representing different views of the anatomy from the treatment gantry angles of the radiotherapy equipment. For example, the software programs 144 may process the set of CT or MR images and create a stack of projection images depicting different views of the anatomy depicted in the CT or MR images from various perspectives of the gantry of the radiotherapy equipment. In particular, one projection image may represent a view of the anatomy from 0 degrees of the gantry, a second projection image may represent a view of the anatomy from 45 degrees of the gantry, and a third projection image may represent a view of the anatomy from 90 degrees of the gantry. The degrees may be directions of the beams relative to a particular axis of the anatomy depicted in the CT or MR images. The axis may remain the same for each beam of the different degrees.

In an example, the software programs 144 may generate graphical aperture image representations of MLC leaf positions at various gantry angles. These graphical aperture images are also referred to as aperture images. In particular, the software programs 144 may receive a set of control points that are used to control a radiotherapy device to produce a shaped radiotherapy beam. The control points may represent the beam intensity, gantry angle relative to the patient position, and the leaf positions of the MLC, among other machine parameters. Based on these control points, a graphical image may be generated to graphically represent the beam shape and intensity that is output by the MLC and jaws at a particular gantry angle. The software programs 144 may align a graphical image of the aperture at a particular gantry angle with the corresponding projection image at that angle that was generated. The images are aligned and scaled with the projections such that the projection image pixel is aligned with the corresponding aperture image pixel.

The software programs 144 may include a treatment planning software. The treatment planning software, when executed such as by a treatment planning system (TPS) can generate the radiation therapy treatment plan 142. In an example, execution of the treatment planning software can produce a graphical aperture image representation of MLC leaf positions at a given gantry angle for a projection image of the anatomy representing the view of the anatomy from the given gantry angle.

As depicted, the software programs 144 may include a beam model 147. The beam model is represented by various characteristics of radiation beams with the imports of a broad radiation field specific to a treatment machine and exiting the radiation therapy machine and impinging upon the patient. Using an appropriately determined beam model, machine parameters or control points for a given type of machine can be calculated, and the radiation therapy machine can output a beam from the MLC that achieves the same or similar estimated graphical aperture image representation of the MLC leaf positions and intensity. The treatment planning software, when executed, may output an image representing an estimated image of the beam shape and the intensity for a given gantry angle and for a given projection image of the gantry at that angle, and the function may compute the control points for a given radiotherapy device to achieve that beam shape and intensity.

The beam model 147 can be represented by a function of one or more beam model types that characterize various properties of one or more radiation modality, such as a photon or an electron. Different beam models may differ in the number and/or configuration of the radiation sources. As such, beam model parameters (e.g., size, position, energy spectrum, or fluence distribution of a radiation source) may vary from one beam model type to another. By way of example and not limitation, the beam model parameters may include size and position of one or more photon sources within the radiation therapy machine, maximum or average energy of a photon spectrum for photons emitted from the radiation therapy machine, factors describing the shape of a photon spectrum emitted from the radiation therapy machine, size and position of one or more electron sources within the radiation therapy machine, maximum or average energy of an electron spectrum emitted from the radiation therapy machine, factors describing the shape of an electron spectrum, or one or more numbers describing how radiation (e.g., electrons or photons) emitted by the radiation therapy machine can vary off-axis, among others.

The AI-based beam modeling technique in accordance with various examples discussed in this document can be applicable to different beam models. An example of the beam model 147 is a full Monte Carlo (MC) model. The full MC model can generate accurate estimates of dose by simulating primary and scattered photons and contamination electrons from the linac head. The full MC model thus can handle complex beam arrangements associated with modern radiotherapy techniques, such as stereotactic body radiotherapy (SBRT), intensity modulated radiotherapy (IMRT), or volumetric modulated arc therapy (VMAT). However, the full MC model can involve a large number of machine components. Detailed modeling of each of the components may require large phase space files (PSFs) to contain vast amount of particle information such as energy, position, direction, charge, regions of creation, or interaction of particles at different scoring planes. The large file size of the PSFs (e.g., as big as several gigabytes) may cause one or more issues related to file storage, reading, deployment, and file transfer (e.g., low speed of reading and transferring PSFs from a hard disk to a local machine). Additionally, the PSFs for a fill MC model may be dependent on precise information about various components in the linac head, such as detailed geometric and material specifications, which can be proprietary information of a manufacturer that is not readily available to a beam modeler.

Figure 4:
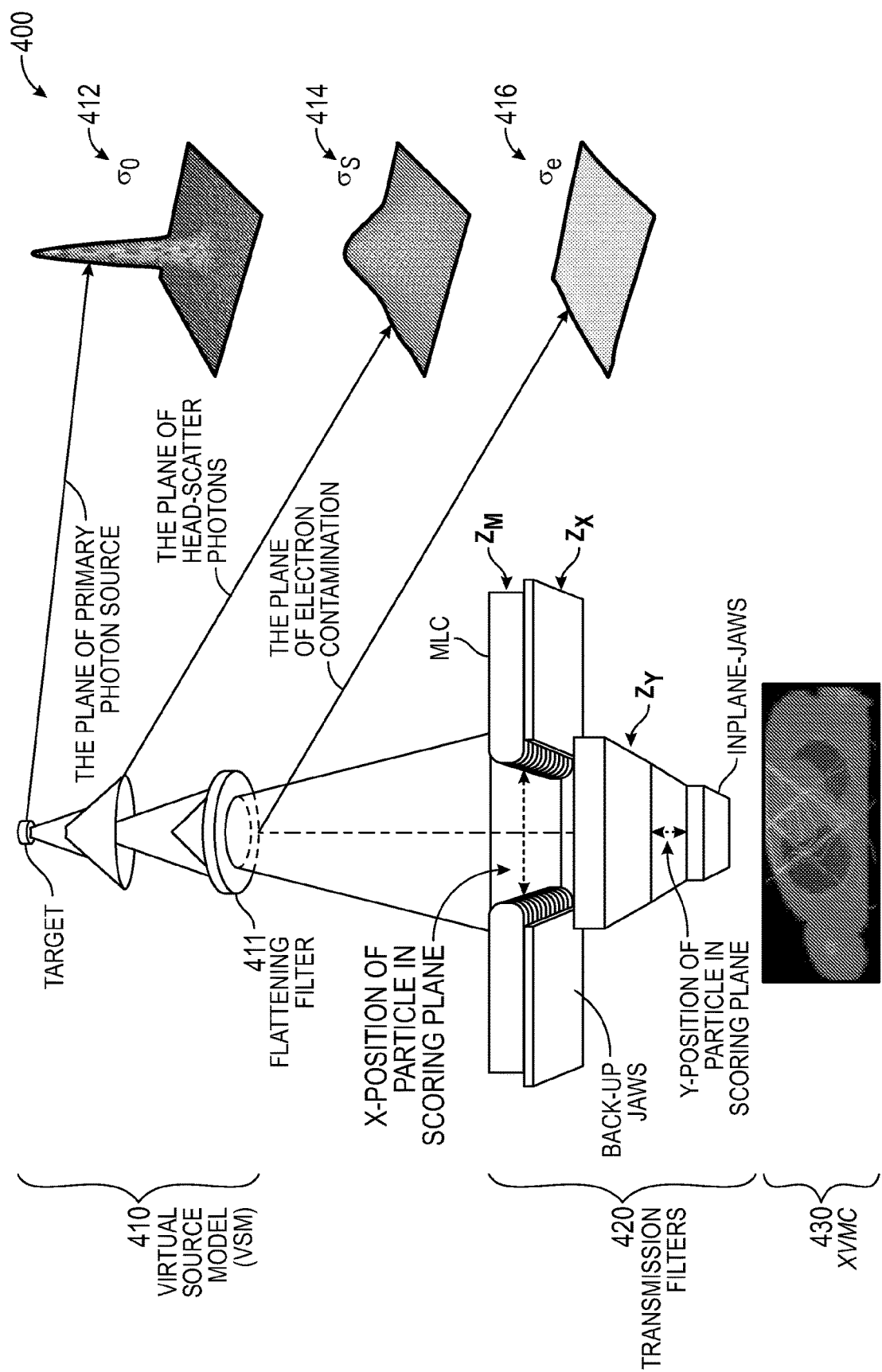
FIG. 4 is a diagram illustrating at least a portion of a Monte Carlo (MC)-based TPS system and a virtual source model (VSM) that may be used for modeling clinical beams.

Another example of the beam model 147 is a virtual source model (VSM), which can approximate a full MC model. Referring now to FIG. 4, which illustrates at least a portion of a Monte Carlo (MC)-based TPS system 400 that employs a VSM to model clinical beams. An MC-based dosimetry algorithm provides the ability to accurately simulate dose distributions within heterogeneous media and thus for clinical situations in radiation therapy. The portion of the MC-based TPS system 400 as depicted comprises a treatment head (e.g., a linac head) 410 and a multi-leaf collimators (MLCs) and jaws 420. The MLCs and jaws 420 can be adjusted to provide individualized radio therapy for a patient and are thus referred to as patient-specific part of the radiation therapy machine. Radiation beams emitted from a radiation source and transport through the treatment head 410 can be modelled by a beam model, such as a VSM. Radiation transport through the MLCs and jaws 420 can be modelled by transmission filters. Medical images 430 (e.g., a CT image) can be produced by the radiation out of the MLC and jaws. From the medical image 430, dose metrics and dose distribution can be calculated based on electronic density of the tissue, such as using a dose engine 152 in the processor 114. Various dose calculation algorithms, based on Monte Carlo techniques, may be used to calculate the dose metrics or distributions, including, for example, voxel Monte Carlo (VMC), or X-ray voxel Monte Carlo (XVMC).

A VSM is a beam model that assumes particles emitted from the linac head are originated from one or more virtual particle sources with different geometries (e.g., point, disc, annulus). Fluence distribution and energy spectrum for each sub-source may be reconstructed either from well-commissioned PSFs or sets of measurements. Specifically, a VSM parametrizes the photon and electron components in linac head, and describes beams with several fitting parameters. The VSM overcomes problems related to full MC simulation of the accelerator head like long simulation time, cumbersome commissioning routine and dependency on the technical information about the accelerator head. As depicted in FIG. 4, a VSM may include two virtual photon sources (representing the contribution from target and flattening filter) and one virtual electron source. Each virtual source of the VSM can generate particle distributions comparable to (with the accuracy required) the dose distribution (e.g., energy and angular distributions) from the original PSFs of the MC model. In particular, the VSM model includes a primary photon source 412, a scatter photon source 414 (also referred to as a secondary photon source), and an electron contamination source 416. The primary photon source 412 can be located in the bremsstrahlung target plane, also referred to as a reference plane with a depth (z) of zero (z=0). The scatter photon source 414 can be located at the base of the primary collimator which, in an example, has depth of approximately z=11.9 cm relative to the reference plane. The electron contamination source 416 can be located at the base of the flattening filter which, in an example, has a depth of approximately z=15.7 cm relative to the reference plane.

A virtual source of the VSM may be described by a respective analytical function of one or more parameters. By way of example and not limitation. FIG. 4 illustrates fluence distributions of respective virtual sources that are modeled by respective Gaussian distribution models. For example, the primary photon fluence may be represented by a Gaussian model with an energy-dependent standard deviation $\sigma_0$, the scatter photon fluence may be represented by a Gaussian model with an energy-dependent standard deviation $\sigma_s$, and the electron fluence may be represented by a Gaussian model with an energy-dependent standard deviation $\sigma_e$. The parameters that describe the virtual sources may include reference parameters fixed based on the full MC data analysis, and open parameters that are fitted during commissioning of the model for each individual accelerator. The photon sources and the electron source in a VSM model may reproduce a variety of effects, which are present in broad clinical beams. Correlations can be computed using these virtual sources, including for example, off-axis energy softening for primary and secondary photons, absorption/scatter in the flattening filter, energy fluence normalization, energy fluence flatness and particle fluence distribution for the primary and secondary photon fluence and electron fluence, energy spectra of the primary and secondary photon sources and the electron source, the correction for energy-focusing of the source distribution for secondary photons and contamination electrons, enhancement of the focus spot particle fluence for contamination electrons, among others. The three virtual sources (i.e., the primary photon, the secondary photon, and the electron contamination) may be independent sources from each other and have a joint probability of one.

Returning now back to FIG. 1, the software programs 144 may include a trained deep learning (DL) model 148 configured to predict values for the model parameters in the beam model 147. The prediction based on machine scanning data indicative of a configuration or an operation status of a radiation therapy machine. The trained DL model 148 is trained to establish a relationship between machine scanning data collected from the radiation therapy machine and a plurality of beam model parameters of a beam model. Machine scanning data corresponding to a radiation therapy machine may be received from a user interface 136 or from the database 124, and applied to the trained DL model 148, which can predict beam model parameters for a beam model. Examples of the trained DL model 148 may include a convolutional neural network (CNN), a recurrent neural network (RNN), a deep belief network (DBN), or a hybrid neural network comprising two or more neural network models of different types or different model configurations.

A CNN network can automatically learn the characteristics of data from samples, eliminating the complex feature extraction in conventional machine learning models which generally requires substantial expert knowledge. Additional advantage of the CNN is that by means of weight sharing, the scale of CNN parameters can be greatly reduced. As a result, the complexity of the training process can be reduced, the converging speed can be increased, and the model generalization ability can be enhanced.

An RNN include connections between nodes to form a directed graph along a temporal sequence. It can use internal state (memory) to store past information, and the network decisions are influenced by what it has learnt from the past. In an example, a long short-term memory (LSTM) network can be used. The LSTM is a type of RNN architecture, characterized by feedback connections. A common LSTM unit can be composed of a cell, an input gate to decide how much new information is to be added to the cell, a forget gate to decide what information is to be discarded or preserved in the cell, and an output gate to decide the values to output.

In an example where the beam model 147 is a virtual source model (VSM). The DL model 148 can be trained to predict values for VSM parameters for one or more virtual sources as depicted in FIG. 4. Examples of a trained CNN for predicting beam model parameters are discussed below, such as with reference to FIGS. 6A-6B.

In addition to the memory 116 storing the software programs 144, the software programs 144 may additionally or alternatively be stored on a removable computer medium, such as a hard drive, a computer disk, a CD-ROM, a DVD, a HD, a Blu-Ray DVD, USB flash drive, a SD card, a memory stick, or any other suitable medium; and the software programs 144 when downloaded to data processing device 112 may be executed by processor 114.

The processor 114 may be communicatively coupled to the memory 116, and the processor 114 may be configured to execute computer executable instructions stored therein. The processor 114 may send or receive medical images 146 to the memory 116. For example, the processor 114 may receive medical images 146 from the image acquisition device 132 via the communication interface 118 and network 120 to be stored in memory 116. The processor 114 may also send medical images 146 stored in memory 116 via the communication interface 118 to the network 120 be stored in the database 124 or the hospital database 126.

The processor 114 may include a training module 151 configured to train a deep learning (DL) model, and to generate the trained DL model 148 to predict beam model parameters, such as VSM parameters. To train the DL model, a training dataset can be constructed using machine scanning data indicative of a configuration or an operation status of a radiation therapy machine (e.g., a linac). The training data may include simulation data, such as dose distributions and dose profiles on a simulation environment (e.g., in a phantom), with known values of beam model parameters and controlled testing conditions. The training module 151 can train the DL model using samples taken from the simulation data and the corresponding known values of the beam model parameters. The training involves algorithmically adjusting one or more DL model parameters (e.g., network layer node weights and biases) until the DL model being trained satisfies a specified training convergence criterion. Examples of training a DL model to predict values of beam model parameters are discussed below with reference to FIG. 5.

The trained DL model 148 can be stored in the memory 116, or the database 124. In an example, the training module 151 and the trained DL model 148 can be archived in a server, and can be accessed by one or more clients (e.g., TPS systems). In some examples, multiple DL models can be trained and archived in a server, corresponding to different multi-leaf collimator (MLC) types (e.g., Agility 160-leaf collimator, or MLCi2 80-leaf collimator, both from Elekta AB of Stockholm, Sweden) and/or different energy levels (e.g., 4, 6, 10, and 15 MV). The DL models archived in the server can be indexed by the MLC types and energy levels. A proper DL model may be queried and retrieved from the server according to the multi-leaf collimator (MLC) type and/or different the energy level.

The processor 114 can generate a beam model 147 for a particular radiation therapy machine (with particular collimator type and/or energy level) using the archived trained DL models. In an example, to generate the beam model 147, the processor 114 can retrieve, from multiple DL models stored archived the server, a trained DL model according to the collimator type and/or energy level associated with the radiation therapy machine. The processor 114 can then apply machine scanning data (e.g., dose curves and dose statistics) acquired from the radiation therapy machine to the retrieved trained DL model, which can produce as output values of a beam model parameters of the beam model 147.

The generated beam model 147 can be stored in the software programs 144. In an example, the beam model 147 may be presented to a user, such as being displayed on the display device 134. Other information may be presented to the user (e.g., displayed on the display device 134), such as a report containing beam model parameters, geometry information, dose calculation settings, and fitting results that show both measured dose distribution and calculated dose distribution based on the beam model. The fitting results. In an example, the beam model 147 may be delivered to a TPS for clinical treatment planning.

In some examples, before a beam model is deploying to a TPS for clinical use, the processor 114 may validate the beam model after the model is generated. The validation may include importing the beam model into a TPS executing a treatment planning software (e.g., Monaco® treatment planning system, manufactured by Elekta AB of Stockholm, Sweden), and calculating the dose distribution in a virtual phantom (e.g., a water phantom). Algorithms for calculating the dose distribution in the virtual phantom may include a Monte Carlo dose algorithm, such as an XVMC algorithm. The calculated dose distribution can be compared to the measured beam characterization from a target radiation therapy machine (e.g., a linac) to determine if the calculated dose satisfies dosimetric verification criteria, also referred to as delivery criteria, such as one or more dose metrics falling within a tolerance range ($\pm x$ %) with respect to the measured dose metrics. Examples of the delivery criteria may include: central ray within $\pm 2$% tolerance, high does at low gradient within a 3% tolerance, high gradient (e.g., 30%/cm) within a 3% tolerance at 3 mm, low dose at low gradient within a 3% tolerance, output factors within a 2% tolerance, or any combination thereof. In some examples, the delivery criteria may include a manual inspection and validation. For example, a modeling physicist can grade the beam model (e.g., the VSM model), such as in a user interface, as one of "Pass" (indicating the model is ready to delivered), "Fail" (indicating the model is unacceptable for delivery), or "Improvement Needed" (indicating further tuning of beam model parameter is needed). The modeling physicist may further add annotations to indicate various characteristics of dose that need to improved, such as spectrum, output factors (OF, at reference depth), buildup region (the range of depth for the attenuation of electron contamination) of PDDs, horn (an increase in beam intensity away from the central axis, dependent mostly on flattening filter design) and penumbra (around the geometric beam edge) of profiles, among others.

The processor 114 may include a dose engine 152 configured to calculate a dose metric or dose statistic using a beam model, such as a VSM model having mode parameters determined by the trained DL model. Various algorithms may be used to calculate the dose. In an example, the dose engine may use a Monte Carlo algorithm or a Collapsed Cone Convolution (CCC) algorithm (which may be implemented as a software package stored in the software programs 144) to calculate the dose metrics or dose statistics. Examples of the dose engine may include a voxel Monte Carlo (VMC) dose engine, an X-ray voxel Monte Carlo (XVMC) dose engine, or a GPU Monte Carlo Dose (GPUMCD).

The processor 114 may include at least a portion of a treatment planning system (TPS) configured to execute a treatment planning software (as part of the software programs 144), and generate the radiation therapy treatment plan 142 using the beam model, the medical images 146, and patient data 145. The medical images 146 may include information such as imaging data associated with a patient anatomical region, organ, or volume of interest segmentation data. The patient data 145 may include information such as: functional organ modeling data (e.g., serial versus parallel organs, appropriate dose response models, etc.); radiation dosage data (e.g., DVH information); or other clinical information about the patient and treatment (e.g., other surgeries, chemotherapy, previous radiotherapy, etc.).

In some examples, the processor 114 may utilize software programs 144 to generate intermediate data such as updated parameters to be used, for example, by a machine learning model, such as a neural network model; or generate intermediate 2D or 3D images, which may then subsequently be stored in memory 116. The processor 114 may subsequently then transmit the executable radiation therapy treatment plan 142 via the communication interface 118 to the network 120 to the radiation therapy device 130, where the radiation therapy plan may be used to treat a patient with radiation. In addition, the processor 114 may execute software programs 144 to implement functions such as image conversion, image segmentation, deep learning, neural networks, and artificial intelligence. For instance, the processor 114 may execute software programs 144 that train or contour a medical image; such software programs 144 when executed may train a boundary detector or utilize a shape dictionary.

The processor 114 may be a processing device, include one or more general-purpose processing devices such as a microprocessor, a central processing unit (CPU), a graphics processing unit (GPU), an accelerated processing unit (APU), or the like. More particularly, the processor 114 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processor 114 may also be implemented by one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some examples, the processor 114 may be a special-purpose processor, rather than a general-purpose processor. The processor 114 may include one or more known processing devices, such as a microprocessor from the Pentium™, Core™. Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processor 114 may also include graphical processing units such as a GPU from the GeForce®, Quadro®, Tesla® family manufactured by Nvidia™, GMA, Iris™ family manufactured by Intel™, or the Radeon™ family manufactured by AMD™. The processor 114 may also include accelerated processing units such as the Xeon Phi™ family manufactured by Intel™. The disclosed examples are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor (for example, a multi-core design or a plurality of processors each having a multi-core design). The processor 114 can execute sequences of computer program instructions, stored in memory 116, to perform various operations, processes, methods that will be explained in greater detail below.

In some examples, various functions performed by the processor 114, such as training of a DL model by the training module 151, generating and validation a beam model, and calculating dose based on beam model using the dose engine 152, can be distributed in two or more processors, or in a client-server architecture. In an example, the training module 151 can be implemented in a server, and the dose engine 152 can be implemented in a client (e.g., a local TPS system). In an example, the trained DL model 148 can be archived in the server.

The memory 116 can store medical images 146. In some examples, the medical images 146 may include one or more MR images (e.g., 2D MRI, 3D MRI, 2D streaming MRI, four-dimensional (4D) MRI, 4D volumetric MRI, 4D cine MRI, etc.), functional MR images (e.g., fMRI, DCE-MRI, diffusion MRI), CT images (e.g., 2D CT, cone beam CT, 3D CT, 4D CT), ultrasound images (e.g., 2D ultrasound, 3D ultrasound, 4D ultrasound), one or more projection images representing views of an anatomy depicted in the MRI, synthetic CT (pseudo-CT), and/or CT images at different angles of a gantry relative to a patient axis, PET images, X-ray images, fluoroscopic images, radiotherapy portal images, SPECT images, computer generated synthetic images (e.g., pseudo-CT images), aperture images, graphical aperture image representations of MLC leaf positions at different gantry angles, and the like. Further, the medical images 146 may also include medical image data, for instance, training images, and ground truth images, contoured images, and dose images. In an example, the medical images 146 may be received from the image acquisition device 132. Accordingly, image acquisition device 132 may include an MRI imaging device, a CT imaging device, a PET imaging device, an ultrasound imaging device, a fluoroscopic device, a SPECT imaging device, an integrated linac and MRI imaging device, or other medical imaging devices for obtaining the medical images of the patient. The medical images 146 may be received and stored in any type of data or any type of format that the data processing device 112 may use to perform operations consistent with the disclosed examples.

The memory 116 may be a non-transitory computer-readable medium, such as a read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a CD-ROM, a DVD or other optical storage, a cassette tape, other magnetic storage device, or any other non-transitory medium that may be used to store information including image, data, or computer executable instructions (e.g., stored in any format) capable of being accessed by the processor 114, or any other type of computer device. The computer program instructions can be accessed by the processor 114, read from the ROM, or any other suitable memory location, and loaded into the RAM for execution by the processor 114. For example, the memory 116 may store one or more software applications. Software applications stored in the memory 116 may include, for example, an operating system 143 for common computer systems as well as for software-controlled devices. Further, the memory 116 may store an entire software application, or only a part of a software application, that are executable by the processor 114. For example, the memory 116 may store one or more radiation therapy treatment plans 142.

The data processing device 112 can communicate with the network 120 via the communication interface 118, which can be communicatively coupled to the processor 114 and the memory 116. The communication interface 118 may provide communication connections between the data processing device 112 and radiotherapy system 100 components (e.g., permitting the exchange of data with external devices). For instance, the communication interface 118 may in some examples have appropriate interfacing circuitry to connect to the user interface 136, which may be a hardware keyboard, a keypad, or a touch screen through which a user may input information into radiotherapy system 100.

Communication interface 118 may include, for example, a network adaptor, a cable connector, a serial connector, a USB connector, a parallel connector, a high-speed data transmission adaptor (e.g., such as fiber. USB 3.0, thunderbolt, and the like), a wireless network adaptor (e.g., such as a WiFi adaptor), a telecommunication adaptor (e.g., 3G, 4G/LTE and the like), and the like. Communication interface 118 may include one or more digital and/or analog communication devices that permit data processing device 112 to communicate with other machines and devices, such as remotely located components, via the network 120.

The network 120 may provide the functionality of a local area network (LAN), a wireless network, a cloud computing environment (e.g., software as a service, platform as a service, infrastructure as a service, etc.), a client-server, a wide area network (WAN), and the like. For example, network 120 may be a LAN or a WAN that may include other systems S1 (138), S2 (140), and S3 (141). Systems S1, S2, and S3 may be identical to data processing device 112 or may be different systems. In some examples, one or more of systems in network 120 may form a distributed computing/simulation environment that collaboratively performs the examples described herein. In some examples, one or more systems S1, S2, and S3 may include a CT scanner that obtains CT images (e.g., medical images 146). In addition, network 120 may be connected to Internet 122 to communicate with servers and clients that reside remotely on the internet.

Therefore, network 120 can allow data transmission between the data processing device 112 and a number of various other systems and devices, such as the OIS 128, the radiation therapy device 130, and the image acquisition device 132. Further, data generated by the OIS 128 and/or the image acquisition device 132 may be stored in the memory 116, the database 124, and/or the hospital database 126. The data may be transmitted/received via network 120, through communication interface 118 in order to be accessed by the processor 114, as required.

The data processing device 112 may communicate with the database 124 through network 120 to send/receive a plurality of various types of data stored on database 124. For example, the database 124 may store machine data associated with a radiation therapy device 130, image acquisition device 132, or other machines relevant to radiotherapy. The machine data information may include control points, such as radiation beam size, are placement, beam on and off time duration, machine parameters, segments. MLC configuration, gantry speed, MRI pulse sequence, and the like. In an example, the database 124 may store training data that may be used to train a DL model for predicting model parameter values for a beam model. The training data may include machine scanning data indicative of a configuration or an operation status of respective radiation therapy machines (e.g., linac machines), and the corresponding actual, measured dose metrics. The database 124 may be a storage device and may be equipped with appropriate database administration software programs. One skilled in the art would appreciate that database 124 may include a plurality of devices located either in a central or a distributed manner.

In some examples, the database 124 may include a processor-readable storage medium (not shown). While the processor-readable storage medium in an example may be a single medium, the term "processor-readable storage medium" should be taken to include a single medium or multiple media (e.g., a centralized or distributed database, and/or associated caches and servers) that store the one or more sets of computer executable instructions or data. The term "processor-readable storage medium" shall also be taken to include any medium that is capable of storing or encoding a set of instructions for execution by a processor and that cause the processor to perform any one or more of the methodologies of the present disclosure. The term "processor readable storage medium" shall accordingly be taken to include, but not be limited to, solid-state memories, optical and magnetic media. For example, the processor readable storage medium can be one or more volatile, non-transitory, or non-volatile tangible computer-readable media.

The processor 114 may communicate with the database 124 to read images into the memory 116, or store images from the memory 116 to the database 124. For example, the database 124 may be configured to store a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DICOM) data, projection images, graphical aperture images, etc.) that the database 124 received from image acquisition device 132. Database 124 may store data to be used by the processor 114 when executing software program 144, or when creating radiation therapy treatment plans 142. The data processing device 112 may receive the imaging data, such as a medical image 146 (e.g., 2D MRI slice images, CT images, 2D Fluoroscopy images, X-ray images, 3DMR images, 4D MR images, projection images, graphical aperture images, etc.) either from the database 124, the radiation therapy device 130 (e.g., an MR-linac), and or the image acquisition device 132 to generate a treatment plan 142.

In an example, the radiotherapy system 100 may include an image acquisition device 132 that can acquire medical images (e.g., MR images, 3D MRI, 2D streaming MRI, 4D volumetric MRI, CT images, cone-Beam CT, PET images, functional MR images (e.g., fMRI, DCE-MRI and diffusion MRI), X-ray images, fluoroscopic image, ultrasound images, radiotherapy portal images. SPECT images, and the like) of the patient. Image acquisition device 132 may, for example, be an MRI imaging device, a CT imaging device, a PET imaging device, an ultrasound device, a fluoroscopic device, a SPECT imaging device, or any other suitable medical imaging device for obtaining one or more medical images of the patient. Images acquired by the image acquisition device 132 can be stored within database 124 as either imaging data and/or test data. By way of example, the images acquired by the image acquisition device 132 can be also stored by the data processing device 112, as medical image 146 in memory 116.

In an example, for example, the image acquisition device 132 may be integrated with the radiation therapy device 130 as a single apparatus. For example, a MR imaging device can be combined with a linear accelerator to form a system referred to as an "MR-linac." Such an MR-linac can be used, for example, to determine a location of a target organ or a target tumor in the patient, so as to direct radiation therapy accurately according to the radiation therapy treatment plan 142 to a predetermined target.

The image acquisition device 132 can be configured to acquire one or more images of the patient's anatomy for a region of interest (e.g., a target organ, a target tumor, or both). Each image, typically a 2D image or slice, may include one or more parameters (e.g., a 2D slice thickness, an orientation, and a location, etc.). In an example, the image acquisition device 132 can acquire a 2D slice in any orientation. For example, an orientation of the 2D slice may include a sagittal orientation, a coronal orientation, or an axial orientation. The processor 114 can adjust one or more parameters, such as the thickness and/or orientation of the 2D slice, to include the target organ and/or target tumor. In an example, 2D slices can be determined from information such as a 3D MRI volume. Such 2D slices can be acquired by the image acquisition device 132 in "real-time" while a patient is undergoing radiation therapy treatment, for example, when using the radiation therapy device 130, with "real-time" meaning acquiring the data in at least milliseconds or less.

The data processing device 112 may generate and store radiation therapy treatment plans 142 for one or more patients. The radiation therapy treatment plans 142 may provide information about a particular radiation dose to be applied to each patient. The radiation therapy treatment plans 142 may also include other radiotherapy information, such as control points including beam angles, gantry angles, beam intensity, dose-histogram-volume (DVH) information, number of radiation beams used during therapy, dose per beam, and the like.

The processor 114 may generate the radiation therapy treatment plan 142 by using software programs 144 such as treatment planning software (e.g., Monaco®, manufactured by Elekta AB of Sweden). In order to generate the radiation therapy treatment plans 142, the processor 114 may communicate with the image acquisition device 132 (e.g., a CT device, an MRI device, a PET device, an X-ray device, an ultrasound device, etc.) to access images of the patient and to delineate a target, such as a tumor. In some examples, the delineation of one or more OARs, such as healthy tissue surrounding the tumor or in close proximity to the tumor may be required. Therefore, segmentation of the OAR may be performed when the OAR is close to the target tumor. In addition, if the target tumor is close to the OAR (e.g., prostate in near proximity to the bladder and rectum), then by segmenting the OAR from the tumor, the radiotherapy system 100 may study the dose distribution not only in the target but also in the OAR.

In order to delineate a target organ or a target tumor from the OAR, medical images, such as MR images, CT images, PET images, fMR images, X-ray images, ultrasound images, radiotherapy portal images, SPECT images, and the like, of the patient undergoing radiotherapy may be obtained non-invasively by the image acquisition device 132 to reveal the internal structure of a body part. Based on the information from the medical images, a 3D structure of the relevant anatomical portion may be obtained. In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible). Other parameters that may be considered include the location of the target organ and the target tumor, the location of the OAR, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker using a program such as Monaco® manufactured by Elekta AB of Sweden) or automatically (e.g., using a program such as the Atlas-based auto-segmentation software, ABAS™, manufactured by Elekta AB of Sweden). In certain examples, the 3D structure of a target tumor or an OAR may be generated automatically by the treatment planning software.

After the target tumor and the OAR(s) have been located and delineated, a dosimetrist, physician, or healthcare worker may determine a dose of radiation to be applied to the target tumor, as well as any maximum amounts of dose that may be received by the OAR proximate to the tumor (e.g., left and right parotid, optic nerves, eyes, lens, inner ears, spinal cord, brain stein, and the like). After the radiation dose is determined for each anatomical structure (e.g., target tumor. OAR), a process known as inverse planning may be performed to determine one or more treatment plan parameters that would achieve the desired radiation dose distribution. Examples of treatment plan parameters include volume delineation parameters (e.g., which define target volumes, contour sensitive structures, etc.), margins around the target tumor and OARs, beam angle selection, collimator settings, and beam-on times. During the inverse-planning process, the physician may define dose constraint parameters that set bounds on how much radiation an OAR may receive (e.g., defining full dose to the tumor target and zero dose to any OAR; defining 95% of dose to the target tumor; defining that the spinal cord, brain stem, and optic structures receive ≤45 Gy, ≤55 Gy and <54 Gy, respectively). The result of inverse planning may constitute a radiation therapy treatment plan 142 that may be stored in memory 116 or database 124. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, the data processing device 112 can generate a tailored radiation therapy treatment plan 142 having these parameters in order for the radiation therapy device 130 to provide radiotherapy treatment to the patient.

In addition, the radiotherapy system 100 may include a display device 134 and a user interface 136. The display device 134 may include one or more display screens that display medical images, interface information, treatment planning parameters (e.g., projection images, graphical aperture images, contours, dosages, beam angles, etc.) treatment plans, a target, localizing a target and/or tracking a target, or any related information to the user. The user interface 136 may be a keyboard, a keypad, a touch screen or any type of device that a user may input information to radiotherapy system 100. Alternatively, the display device 134 and the user interface 136 may be integrated into a device such as a tablet computer.

Furthermore, any and all components of the radiotherapy system 100 may be implemented as a virtual machine (e.g., VMWare, Hyper-V, and the like). For instance, a virtual machine can be software that functions as hardware. Therefore, a virtual machine may include at least one or more virtual processors, one or more virtual memories, and one or more virtual communication interfaces that together function as hardware. For example, the data processing device 112, the OIS 128, the image acquisition device 132 could be implemented as a virtual machine. Given the processing power, memory, and computational capability available, the entire radiotherapy system 100 could be implemented as a virtual machine.

Figure 2A:
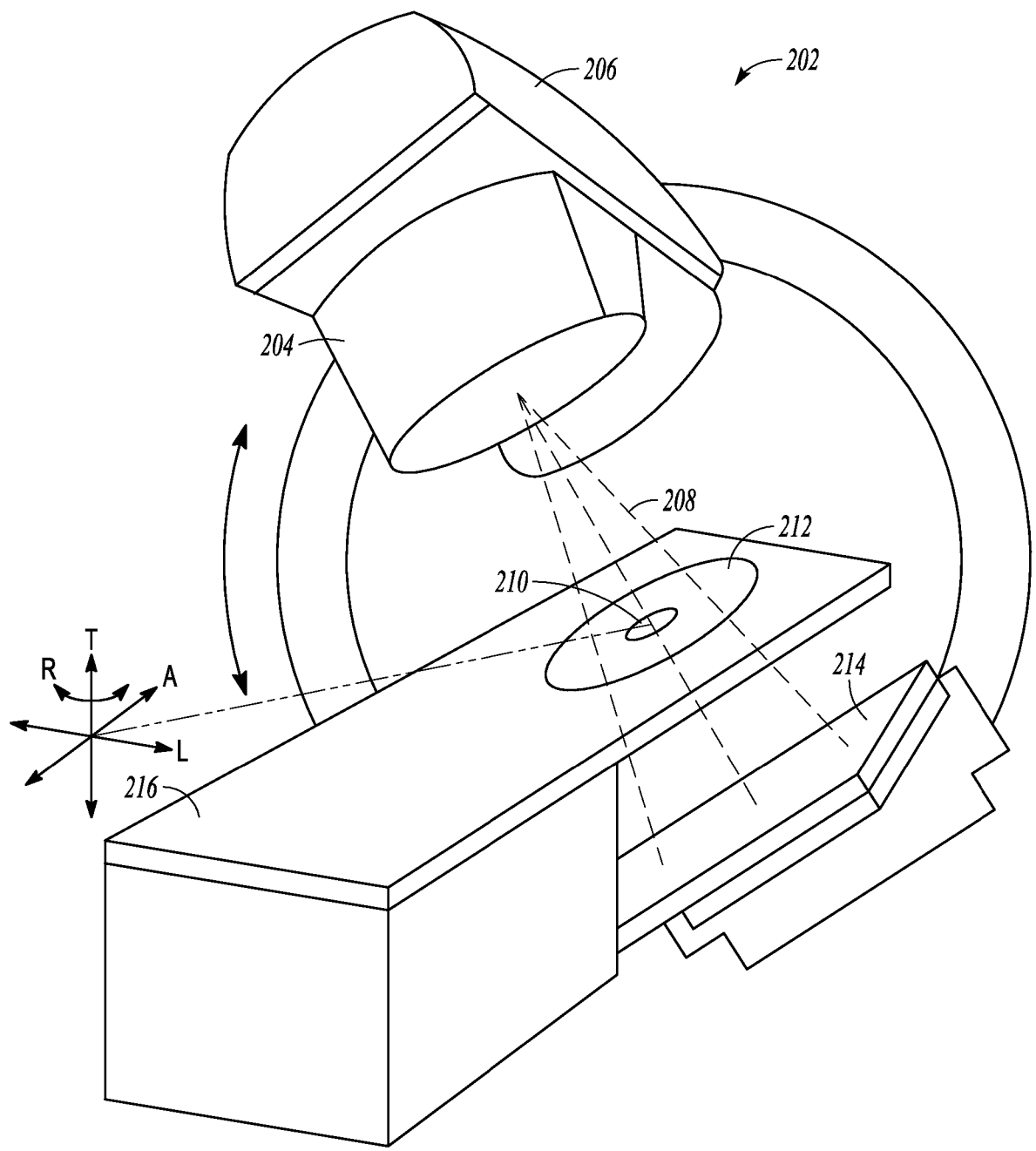
FIG. 2A illustrates an exemplary radiotherapy system that can provide a therapy beam.

FIG. 2A illustrates an exemplary radiation therapy device 202 that may include a radiation source (e.g., an X-ray source or a linac), a couch 216, an imaging detector 214, and a radiation therapy output 204. The radiation therapy device 202 may be configured to emit a radiation beam 208 to provide therapy to a patient. The radiation therapy output 204 may include one or more attenuators or collimators, such as an MLC. A patient can be positioned in a region 212 and supported by the couch 216 to receive a radiation therapy dose, according to a radiation therapy treatment plan. The radiation therapy output 204 can be mounted or attached to a gantry 206 or other mechanical support. One or more chassis motors (not shown) may rotate the gantry 206 and the radiation therapy output 204 around the couch 216 when the couch 216 is inserted into the treatment area. In an example, the gantry 206 may be continuously rotatable around the couch 216 when the couch 216 is inserted into the treatment area. In another example, the gantry 206 may rotate to a predetermined position when the couch 216 is inserted into the treatment area. For example, the gantry 206 can be configured to rotate the therapy output 204 around an axis ("A"). The couch 216 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 216 movements or rotations in order to properly position the patient in or out of the radiation beam 208 according to a radiation therapy treatment plan. Both the couch 216 and the gantry 206 are independently moveable from one another in multiple degrees of freedom, which allows the patient to be positioned such that the radiation beam 208 can target the tumor. The MLC may be integrated with the gantry 206 to deliver the radiation beam 208 of a certain shape.

The coordinate system (including axes A, 7 and L) shown in FIG. 2A can have an origin located at an isocenter 210. The isocenter can be defined as a location where the central axis of the radiation beam 208 intersects the origin of a coordinate axis, such as to deliver a prescribed radiation dose to a location on or within a patient. Alternatively, the isocenter 210 can be defined as a location where the central axis of the radiation beam 208 intersects the patient for various rotational positions of the radiation therapy output 204 as positioned by the gantry 206 around the axis A. As discussed herein, the gantry angle corresponds to the position of gantry 206 relative to axis A, although any other axis or combination of axes can be referenced and used to determine the gantry angle.

The linac system may have an imaging detector 214 that is preferably opposite the radiation therapy output 204. In an example, the imaging detector 214 can be located within a field of the therapy beam 208. The imaging detector 214 can maintain alignment with the therapy beam 208. The imaging detector 214 can rotate about the rotational axis as the gantry 206 rotates. In an example, the imaging detector 214 can be a flat panel detector (e.g., a direct detector or a scintillator detector). In this manner, the imaging detector 214 can monitor the therapy beam 208, or generate an image of the patient's anatomy. The control circuitry of radiotherapy device 202 may be integrated within system 100 or remote from it.

In an illustrative example, one or more of the couch 216, the therapy output 204, or the gantry 206 can be automatically positioned, and the therapy output 204 can establish the therapy beam 208 according to a specified dose for a particular therapy delivery instance. A sequence of therapy deliveries can be specified according to a radiation therapy treatment plan, such as using one or more different orientations or locations of the gantry 206, the couch 216, or the therapy output 204. The therapy deliveries can occur sequentially, but can intersect in a desired therapy locus on or within the patient, such as at the isocenter 210. A prescribed dose of radiation therapy can thereby be delivered to the therapy locus while damage to tissue near the therapy locus can be reduced or avoided.

Figure 2B:
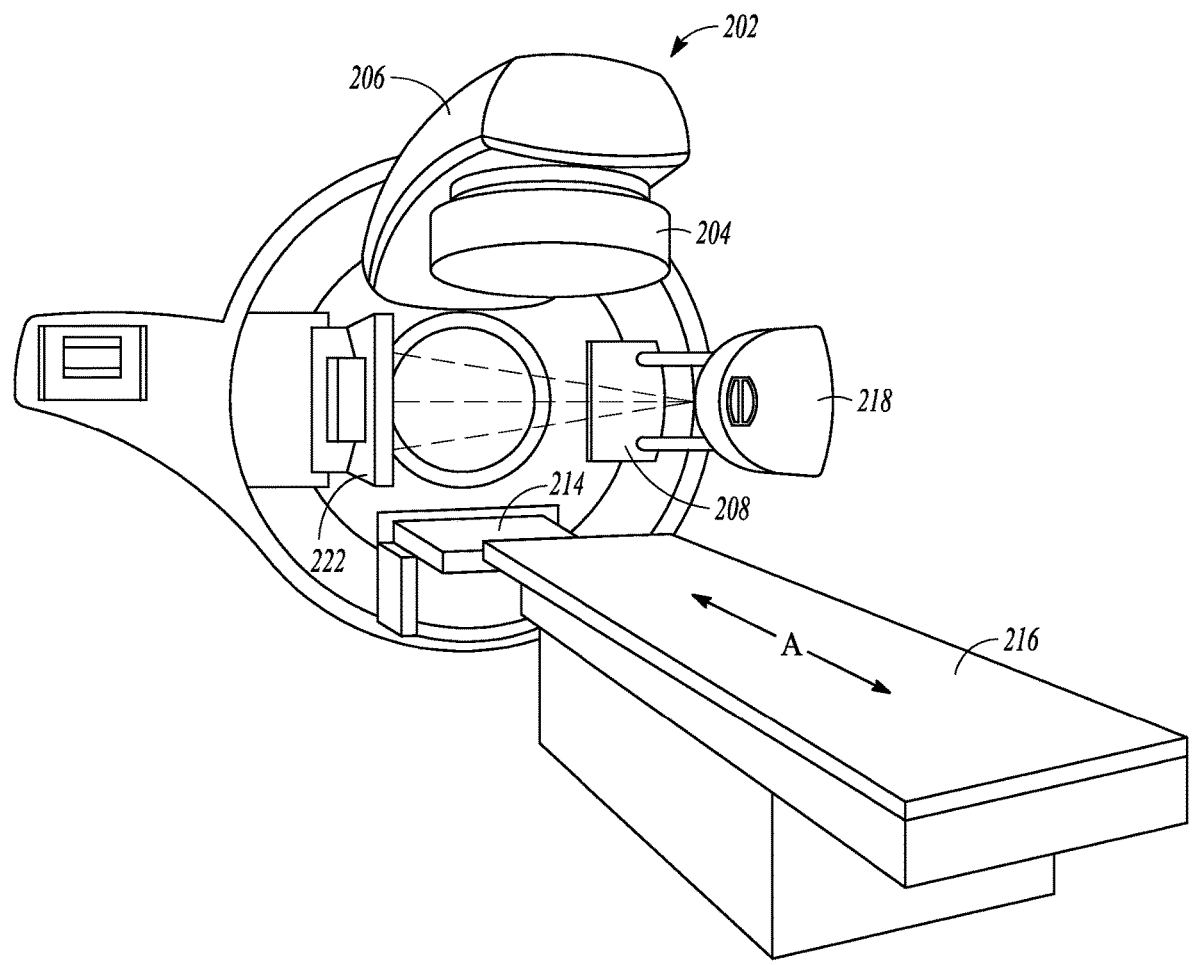
FIG. 2B illustrates an exemplary combined system including a computed tomography (CT) imaging system and a radiation therapy system.

FIG. 2B illustrates an exemplary radiotherapy system 202 that combines a radiation system (e.g., a linac) and a CT imaging system. The radiation therapy output 204 may include an MLC (not shown). The CT imaging system may include an imaging X-ray source 218, such as providing X-ray energy in a kiloelectron-Volt (keV) energy range. The imaging X-ray source 218 can provide a fan-shaped and/or a conical beam 208 directed to an imaging detector 222, such as a flat panel detector. The radiation therapy device 202 can be similar to the system described in relation to FIG. 2A, such as including a radiation therapy output 204, a gantry 206, a couch 216, and another imaging detector 214 (such as a flat panel detector). The X-ray source 218 can provide a comparatively-lower-energy X-ray diagnostic beam, for imaging.

As illustrated in FIG. 2B, the radiation therapy output 204 and the X-ray source 218 can be mounted on the same rotating rotation mechanism, rotationally-separated from each other by 90 degrees. In some examples, two or more X-ray sources can be mounted along the circumference of the rotation mechanism, such that each has its own detector arrangement to provide multiple angles of diagnostic imaging concurrently. Similarly, multiple radiation therapy outputs 204 may be provided.

Figure 3:
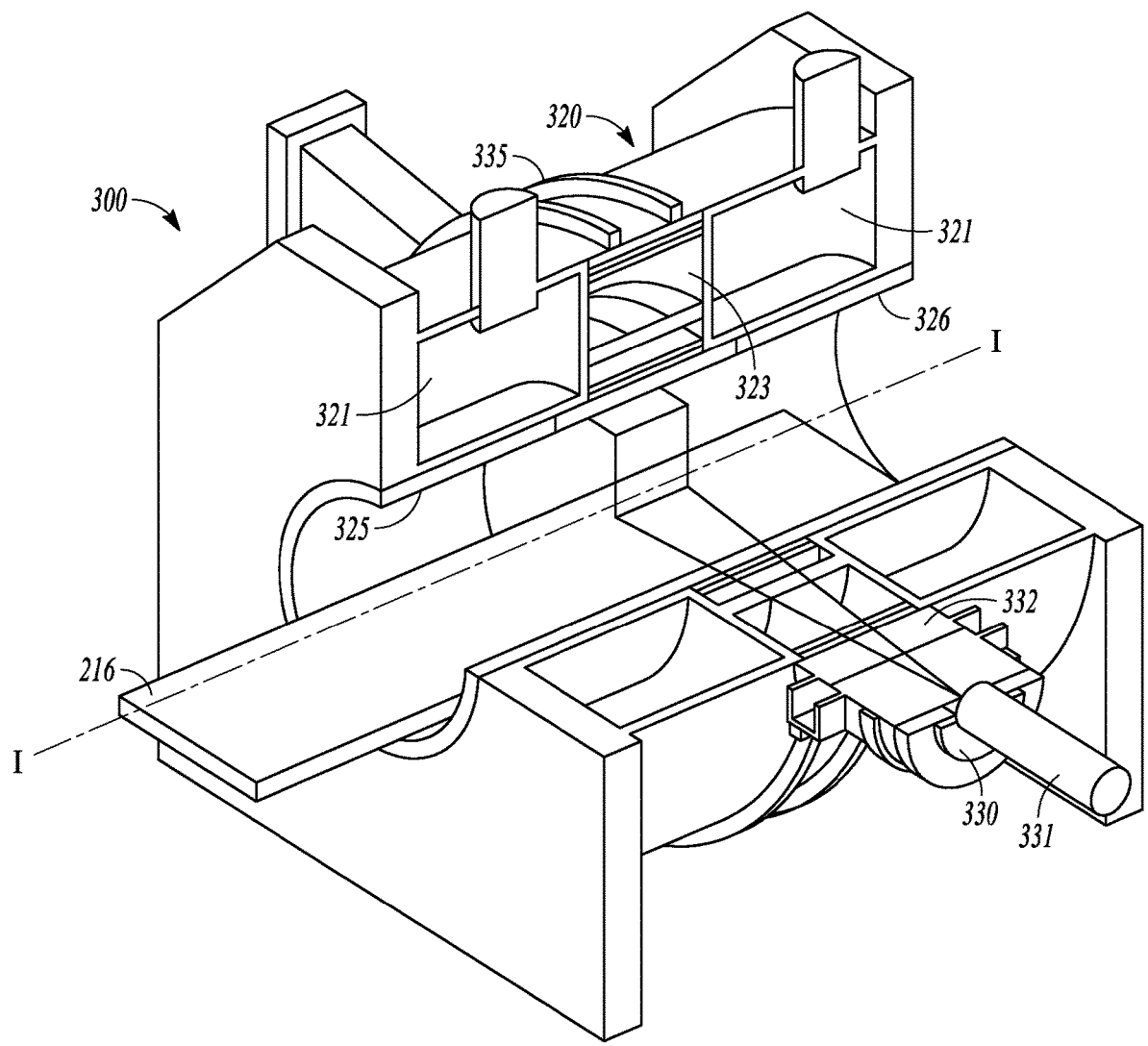
FIG. 3 illustrates a partially cut-away view of an exemplary combined system including a nuclear magnetic resonance (MR) imaging system and a radiation therapy system.

FIG. 3 illustrates an exemplary radiotherapy system 300 that combines a radiation system (e.g., a linac) and a nuclear MR imaging system, also referred to as an MR-linac system. The system 300 may include a couch 216, an image acquisition device 320, and a radiation delivery device 330. The system 300 can deliver radiation therapy to a patient in accordance with a radiotherapy treatment plan, such as the treatment plan 142 generated and stored in the memory 116. In some examples, the image acquisition device 320 may correspond to the image acquisition device 132 in FIG. 1 that may acquire images of a first modality (e.g., an MR image) or destination images of a second modality (e.g., a CT image).

The couch 216 may support a patient during a treatment session. In some implementations, the couch 216 may move along a horizontal translation axis (labelled "I"), such that the couch 216 can move the patient resting on the couch 216 into and/or out of the system 300. The couch 216 may also rotate around a central vertical axis of rotation, transverse to the translation axis. To allow such movement or rotation, the couch 216 may have motors (not shown) enabling movement of the couch 216. A controller (not shown) may control these movements or rotations in order to properly position the patient according to a treatment plan.

In some examples, the image acquisition device 320 may include an MR imaging machine that can acquire 2D or 3D MR images of the patient before, during, and/or after a treatment session. The image acquisition device 320 may include a magnet 321 for generating a primary magnetic field for magnetic resonance imaging. The magnetic field lines generated by operation of the magnet 321 may run substantially parallel to the central translation axis "I". The magnet 321 may include one or more coils with an axis that runs parallel to the translation axis "I". In some examples, the one or more coils in magnet 321 may be spaced such that a central window 323 of magnet 321 is free of coils. In other examples, the coils in magnet 321 may be thin enough or of a reduced density such that they are substantially transparent to radiation of the wavelength generated by radiotherapy device 330. In some examples, the image acquisition device 320 may also include one or more shielding coils, which may generate a magnetic field outside the magnet 321 of approximately equal magnitude and opposite polarity in order to cancel or reduce any magnetic field outside of the magnet 321. As described below, a radiation source 331 of radiotherapy device 330 may be positioned in the region where the magnetic field is cancelled, at least to a first order, or reduced.

The image acquisition device 320 may also include two gradient coils 325 and 326, which may generate a gradient magnetic field that is superposed on the primary magnetic field. The coils 325 and 326 may generate a gradient in the resultant magnetic field that allows spatial encoding of the protons so that their position can be determined. The gradient coils 325 and 326 may be positioned around a common central axis with the magnet 321 and may be displaced along that central axis. The displacement may create a gap, or window, between the coils 325 and 326. In examples where the magnet 321 includes a central window 323 between the coils, the two windows may be aligned with each other.

In some examples, the image acquisition device 320 may be an imaging device other than an MRI, such as an X-ray, a CT, a CBCT, a spiral CT, a PET, a SPECT, an optical tomography, a fluorescence imaging, ultrasound imaging, radiotherapy portal imaging device, or the like. As would be recognized by one of ordinary skill in the art, the above description of image acquisition device 320 concerns certain examples and is not intended to be limiting.

The radiotherapy device 330 may include the radiation source 331 (e.g., an X-ray source or a linac), and a collimator such as an MLC 332. A collimator is a beam-limiting device that can help to shape the beam of radiation emerging from the machine and can limit the maximum field size of a beam. The MLC 332 can be used for shaping, directing, or modulating an intensity of a radiation therapy beam to the specified target locus within the patient. The MLC 332 may include metal collimator plates, also known as MLC leaves, which slide into place to form the desired field shape. The radiotherapy device 330 may be mounted on a chassis 335. One or more chassis motors (not shown) may rotate chassis 335 around the couch 216 when the couch 216 is inserted into the treatment area. In an example, chassis 335 may be continuously rotatable around the couch 216, when the couch 216 is inserted into the treatment area. The chassis 335 may also have an attached radiation detector (not shown), preferably located opposite to radiation source 331 and with the rotational axis of chassis 335 positioned between radiation source 331 and the detector. Further, device 330 may include control circuitry (not shown) used to control, for example, one or more of the couch 216, image acquisition device 320, and radiotherapy device 330. The control circuitry of radiotherapy device 330 may be integrated within system 300 or remote from it.

During a radiotherapy treatment session, a patient may be positioned on the couch 216. System 300 may then move the couch 216 into the treatment area defined by magnetic 321 and coils 325, 326, and chassis 335. Control circuitry may then control the radiation source 331. MLC 332, and the chassis motor(s) to deliver radiation to the patient through the window between coils 325 and 326 according to a radiotherapy treatment plan.

The radiation therapy output configurations illustrated in FIGS. 2A-2B and 3, such as the configurations where a radiation therapy output can be rotated around a central axis (e.g., an axis "A"), are for the purpose of illustration and not limitation. Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a platform supporting the patient can be used to align a radiation therapy isocenter with a specified target locus within the patient.

Figure 5:
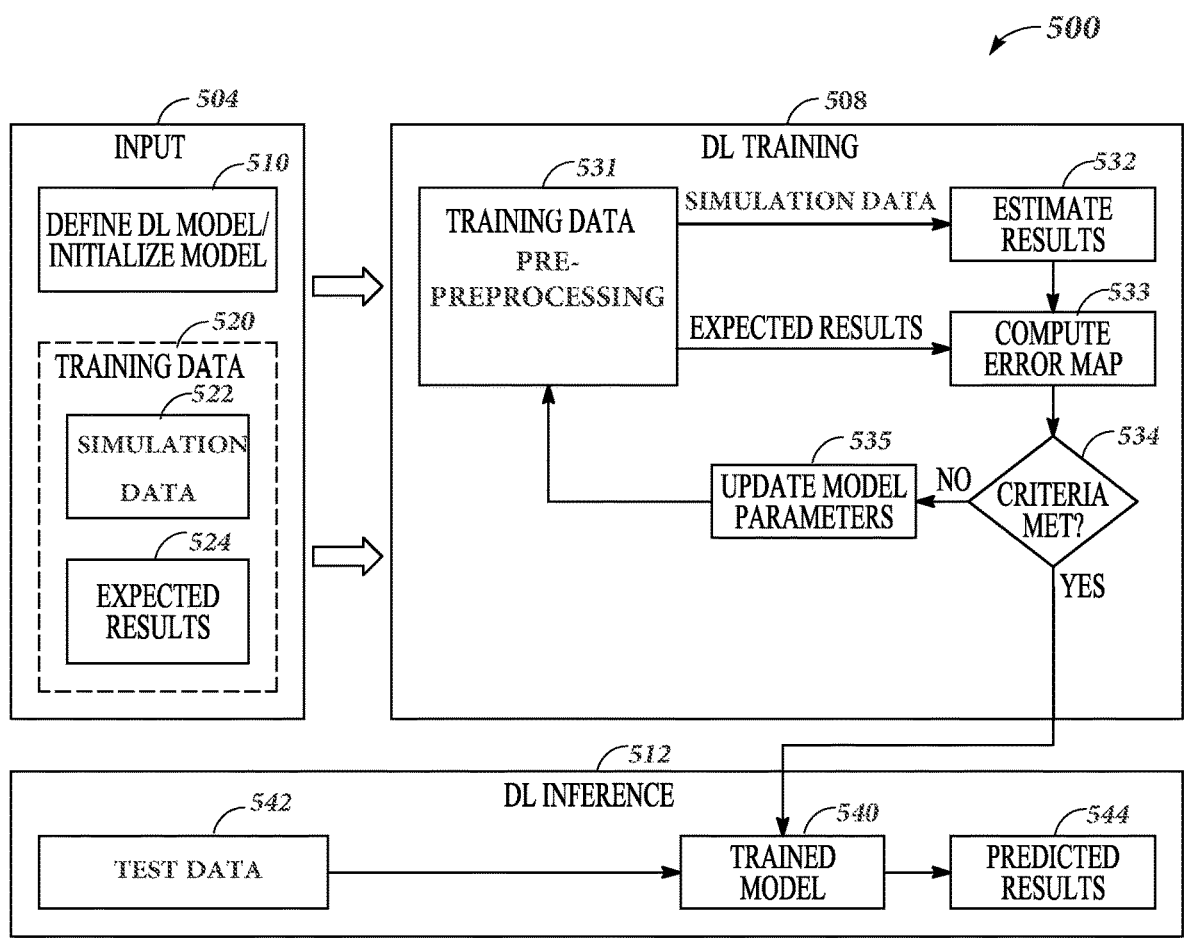
FIG. 5 is a block diagram illustrating an exemplary process for training a deep learning (DL) model for predicting beam model parameters in a beam model.

FIG. 5 is a diagram illustrating an exemplary process 500 for training a deep learning (DL) model that can predict beam model parameter values for a beam model, such as the beam model 147. The process 500 can be implemented as computer-readable and executable instructions and executed by the training module 151. Input 504 may include a DL model 510 having an initial network architecture and initial parameter settings. Examples of the DL model 510 may include a convolutional neural network (CNN), a recurrent neural network (RNN), a deep belief network (DBN), or a hybrid neural network comprising two or more neural network, models of different types or different model configurations. Examples of a CNN model for predicting model parameter values are described below, such as with reference to FIGS. 6A-6B.

The input 504 may include training data 520 that may be used for training the DL model 510. As depicted, the training data 520 may include simulation data 522 and the expected results 524. The simulation data 522 is the input to the DL model, and the expected results 524 are corresponding desired output (or "target labels") of the DL model. The simulation data 522 may include simulated machine scanning data representing characteristics of the beams from a radiation therapy machine such as a linac head. Examples of the machine scanning data may include a percentage depth dose (PDD) that characterizes relative dose quantity determined as the ratio between the axis dose at a specific depth (z, such as within a range of 0-30) mm) and the axis dose at a reference dose depth ($z_0$); a dose profile (or a dose distribution) that characterizes off-axis dose distribution, such as doses at diagonals, a percentage radial dose (PRD) profile representing changes of relative dose with a radial distance; a dose-volume histogram; an overlap volume histogram; or a three-dimensional dose distribution, among others.

The machine simulation data 522 may be generated using a dose engine in the software programs 144, during a radiation simulation where the radiation therapy machine is configured with beam model parameters {X} with known values X=X*. During the simulation, radiation beams from the radiation therapy machine may be applied to a phantom (e.g., a virtual water phantom). Scanning data (e.g., PPD and dose profiles) can be measured at various depths in a phantom, such as multiple depths between 0-30 centimeters (cm). At a particular depth (e.g., z=5 cm), scanning data can be measured within one or more field sizes (e.g., 2×2, 3×3, 5×5, 10×10, 20×20, or 40×40 $cm^2$). In some examples, machine simulation data may be generated for each of a set of beam energy levels, such as 4, 6, 10, and 15 MV.

In some examples, the training data 520 may additionally include machine settings data including information about settings of the radiation therapy machine. Examples of the machine settings data may include: linac setting and geometry information, such as position and thickness of jaw collimators and MLC; thickness, position, shape (perimeter and edge), and composition of each applicator; thickness, shape, and composition for each insert; position of gantry; position of gantry, among others. The machine settings data may also include: general information about the radiation therapy machine, such as linac model, serial number, MLC model and modality, among others, among others.

The expected results 524 may include beam model parameters {X} with known values X=X*. Examples of the beam model parameters may include a size and position of one or more photon sources within the radiation therapy machine, a maximum energy of a photon spectrum for photons emitted from the radiation therapy machine, a number of factors describing the shape of a photon spectrum emitted from the radiation therapy machine, a size and position of one or more electron sources within the radiation therapy machine, an average energy of an electron spectrum emitted from the radiation therapy machine, or one or more numbers describing how radiation (e.g., electrons or photons) emitted by the radiation therapy machine can vary off-axis, among others.

The simulation data 522 can be collected during dose simulations under different testing conditions as the beam model parameters {X} are set to respective known values. In an example, the radiation therapy machine can deliver radiation during a simulation without the applicator and with collimator jaws wide open. The machine scanning data collected under this testing condition are referred to as open-field measurements. Examples of the open-filed measurements may include absolute dose (reference dose) at a specific point on the depth-dose curve, dose profiles in air at a specific source to detector distance (SDD), depth-dose curves in water at a specific SSD. In an example, the SSD is approximately 100 cm. In another example, applicator can be used during a dose simulation. The machine scanning data collected under such a testing condition are referred to as applicator measurements. In an example, the applicator measurements can be performed for each energy/applicator combination, including absolute dose (reference dose) at a specific point on the depth-dose curve, depth-dose curves in water at a specific SSD, among others. Machine scanning data (e.g., PDD and dose profiles) may be collected in an open-field and applicator combinations for each beam energy, where the measurements are taken in air and/or in water at multiple depths.

Figure 7A:
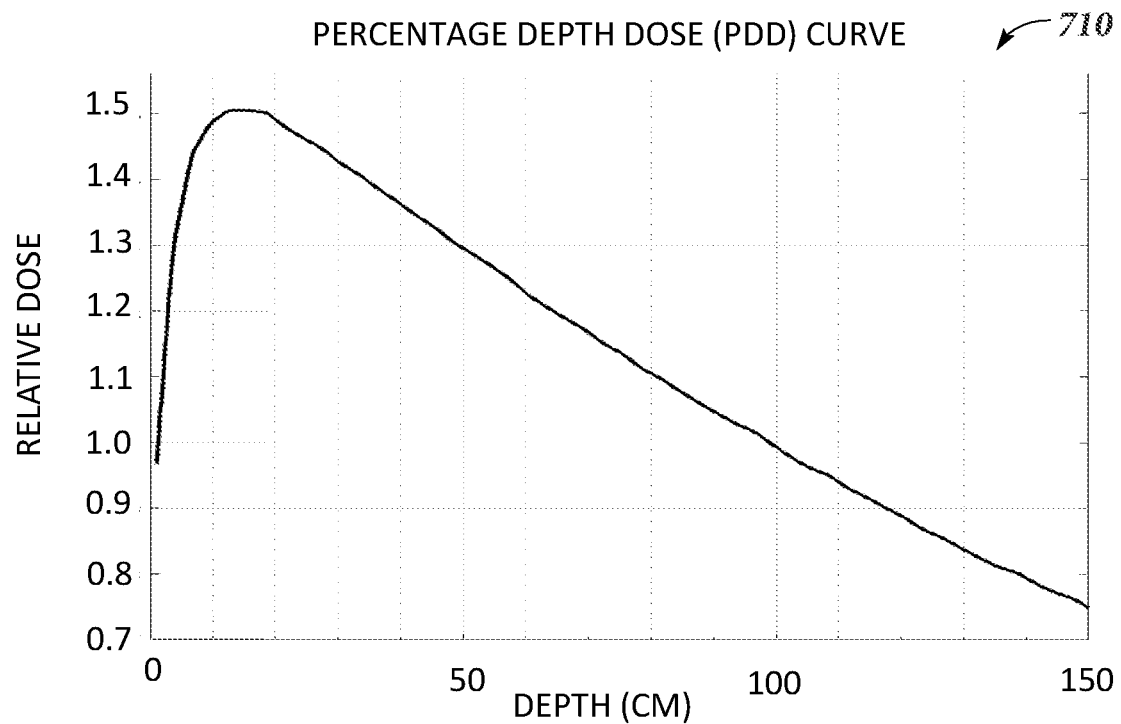
FIGS. 7A-7E are diagrams illustrating examples of dose characteristics generated based on measurements of scanning data during a radiation simulation.
Figure 7B:
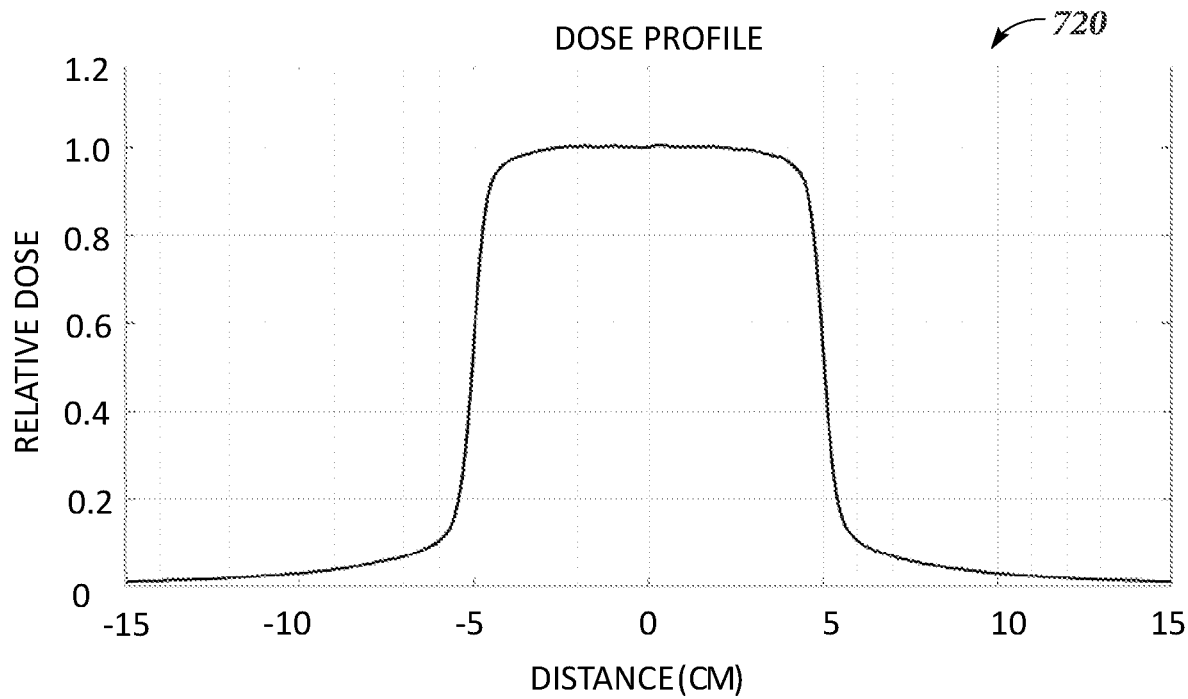

Referring to FIGS. 7A-7E, the diagrams therein illustrate beam characteristics, such as percentage depth dose (PDD) curves or dose profiles, based on scanning data measured during a simulation, such as in a phantom (e.g., water phantom). FIG. 7A illustrates an exemplary PDD curve 710. The amount of radiation deposited, as a function of depth in the medium, can be measured using sensors installed in the phantom. The PDD curve represents dose measurements at different depths normalized to a point dose with a reference field size (e.g., 10×10 $cm^2$) at the reference depth (e.g., 10 cm). FIG. 7B illustrates an exemplary dose profile 720. A dose profile is an off-axis dose distribution represented by relative dose measurements at locations with different distances from the central axis of the beam, normalized to the dose value at a reference depth and a reference field size. For each dose profile, dose values may be measured at a specific depth (z) within a specific field size. By way of example, the dose profile 720 represents a dose distribution corresponding to a depth of z=10 cm and a field size of 10×10 $cm^2$ on the x-axis of the phantom.

Figure 7C:
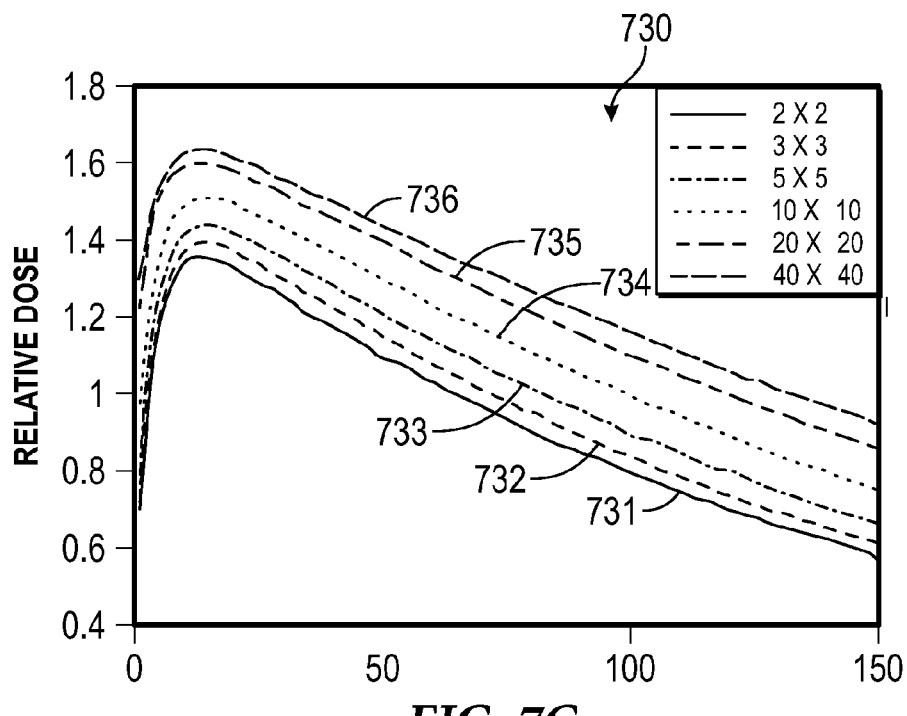
Figure 7D:
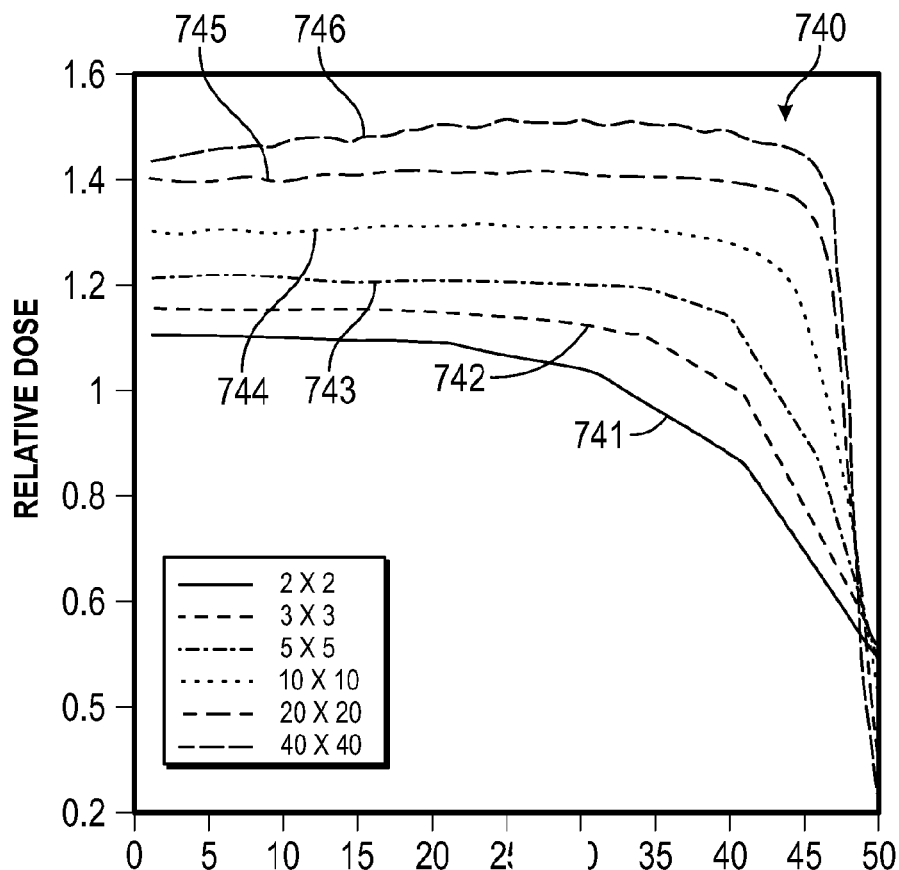

Dose characteristics (e.g., PDD curves or dose profiles) may be generated using dose measurements or simulation corresponding to multiple, different field sizes. Simulated dose data may be used to construct a 2D dose value matrix containing dose characteristics (e.g., PDD curves or dose profiles) that may be used to train the DL model. PDD curves or dose profiles with different types or field sizes may be sampled with their individual sampling rate to form the 2D matrix. In an example, a dose profile corresponding to a field size of 2×2 $cm^2$ may be sampled at a resolution of 0.2 mm. In an example, a dose profile corresponding to a field size of 3×3 $cm^2$ may be sampled at a resolution of 0.3 mm. By way of example and not limitation, FIG. 7C illustrates an overlay plot 730 of multiple one-dimensional (1D) relative dose arrays sampled from respective PDD curves, referred to as sampled PDDs 731-736. FIG. 7D illustrates an overlay plot 740 of multiple (1D relative dose arrays sampled from dose profiles at a specified depth (e.g., 5 cm on the x-axis of phantom), referred to as sampled dose profiles 741-746. Only the portions of dose profiles with positive locations (i.e., distances greater than zero) are shown in FIG. 7D. Sampled PDD 731 and dose profile 741 correspond to a field size of 2×2 $cm^2$. Sampled PDD 732 and sampled dose profile 742 correspond to a field size of 3×3 $cm^2$. Sampled PDD 733 and sampled dose profile 743 correspond to a field size of 5×5 cm. Sampled PDD 734 and sampled dose profile 744 correspond to a field size of 10×10 $cm^2$. Sampled PDD 735 and sampled dose profile 745 correspond to a field size of 20×20 cm. Sampled PDD 736 and sampled dose profile 746 correspond to a field size of 40×40 $cm^2$. In both FIGS. 7C and 7D, the y-axis represents relative dose values, and the x-axis represents indices of the relative dose array. The relative dose values at the depths that numerical indices represent are sampled using interpolation or extrapolation. The relative dose values from multiple sampled PDDs 731-736, or from multiple sampled dose profiles 741-746, can be constructed into a data array, such as a two-dimensional (2D) dose value matrix. The sampled PDDs and the sampled dose profiles with the same field size may be combined into one curve. The 2D dose value matrix has a first dimension representing different sampling positions, and a second dimension representing different field sizes. The resulting 2D dose value matrix may be used as the training data to train the DL model 510.

Figure 7E:
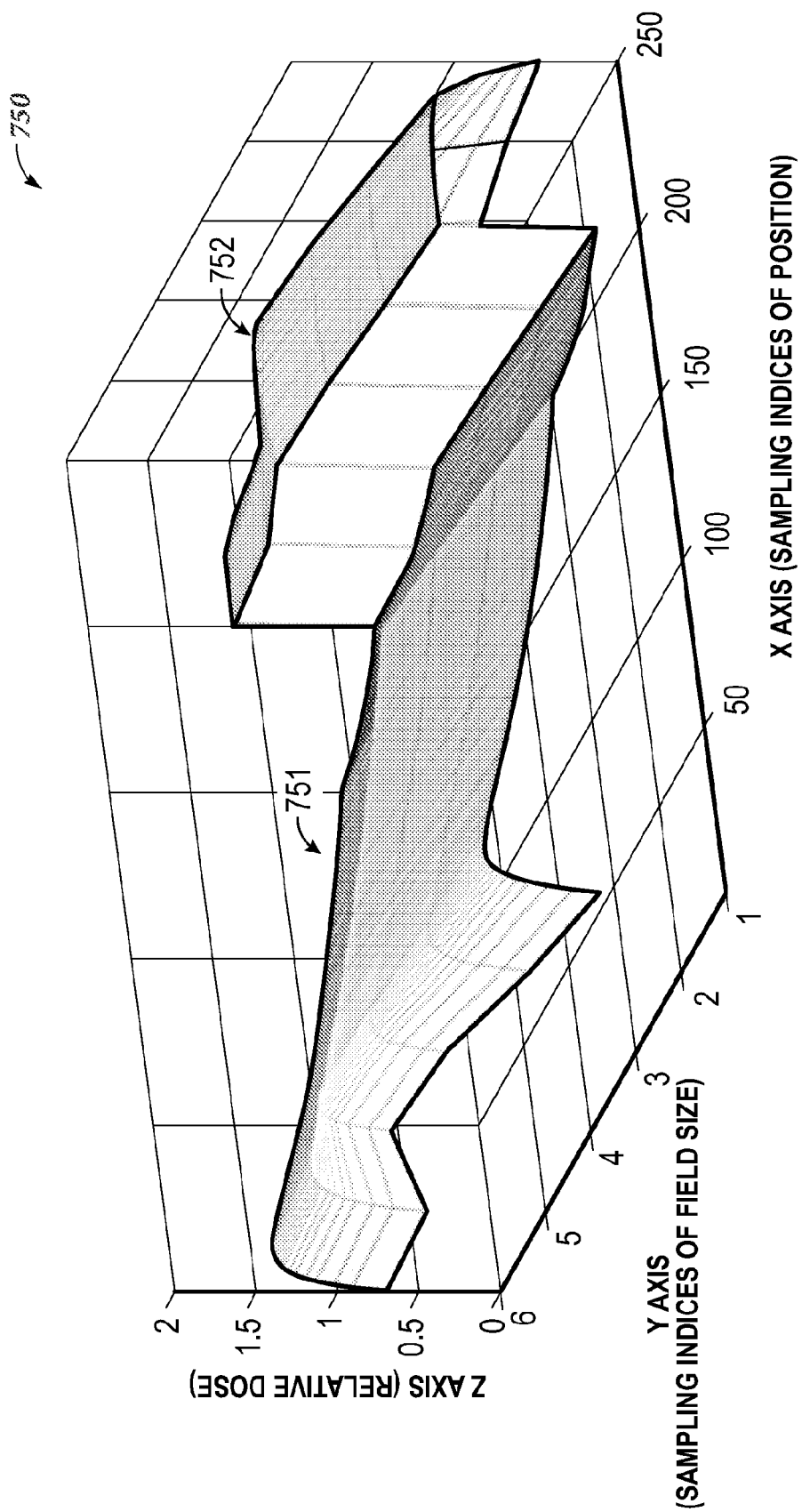

Training a DL model may require a large amount of training data. While more simulations may produce more training data, they also lengthen the simulation time and add computation complexity. The present document describes, among other things, a method of generating additional training data without performing excessive simulations. The method is based on interpolating and/or extrapolating the simulation data obtained from a simulation and organized in a 2D dose value matrix. FIG. 7E illustrates a surface plot 750 representing relative dose values over a range of field sizes and over a range of positions. The z-axis of the surface plot 750 represents relative dose values, the y-axis represents sampling indices of field size, and the x-axis represents sampling indices of positions. The relative dose values can be represented by a 2D dose matrix. As depicted, the surface plot 750 includes a first portion 751 and a second portion 752. The dose values on the first portion 751 can be represented by a first 2D dose matrix, created by interpolating and/or extrapolating relative dose values between at least two PDD curves. The dose values on the second portion 752 can be represented by a second 2D dose matrix created by interpolating and/or extrapolating relative dose values between at least two dose profiles. Examples of interpolation can include linear interpolation, nearest neighbor interpolation, polynomial interpolation, or spline interpolation, among others. The interpolation and/or extrapolation of relative dose values can be performed over the dose values at a finer resolution of depth (z) and/or a finer resolution of field size. In Sone examples, the interpolated first and second 2D dose matrices each may have a non-uniformed resolution of depth. For example, for depths between 0 and 150 mm, the PDD (the first dose matrix) may be linearly interpolated with a resolution of 1 mm; and for depths from 151 to 300 mm, the PDD (the first 2D dose matrix) may be linearly interpolated with a resolution of 3 mm. In an example, the dose profiles (the second 2D dose matrix) may be interpolated with a resolution according to its field size. For example, for a field size of 2×2 cm², the resolution of field size may be approximately 0.2 mm. As such, the interpolated/extrapolated first and second 2D dose matrices each represent dose values calculated for a range of positions and a range of field sizes with respective finer resolutions. The interpolated/extrapolated first and second 2D dose matrices may be concatenated. A specific number (e.g., 3000-5000) of concatenated 2D dose matrices may be used as training data to train the DL model. In an example, the training module 151 may sample the dose characteristics to the concatenated 2D dose matrix at a specified sampling resolution. The concatenated 2D dosed matrix may include the interpolated dose values. In an example, the sampling resolution may be chosen according to the field size.

In an example, the beam model includes a VSM, such as described above with reference to FIG. 4. During a dose simulation, the VSM is programmed with known values for a plurality of VSM parameters, $X_{VSM}=X_{VSM}^*$. The simulated machine scanning data (e.g., PPD and dose profiles) can be generated while varying only a subset of VSM parameters, and keeping other VSM parameters at their respect default values for a same type of linac with the same MLC type (i.e., unchanged throughout the dose simulation). Examples of the subset of VSM parameters that are varied to generate the simulation data may include: output factors (OF) parameters including primary photon, primary sigma, scatter distance, scatter sigma; spectral parameters including energy max, energy min. B-value, secondary B-value; and build-up region parameters including charged particle, charged radius, charged mean energy $E_{mean}$, charged maximum energy $E_{max}$, among others. In an example, at least some of the subset of the VSM parameters may be randomly combined, and the simulation data 522 can be generated corresponding to the randomly combined VSM parameters. In an example, probability distributions of the VSM parameters can be analyzed, and the simulation data 522 can be generated corresponding to a set of VSM parameters based on their respective probability distributions.

Referring now back to FIG. 5, the DL training process 508 can apply the training data 520 to train the DL model 510. In an example, the DL training process 508 can be implemented in a first device, such as a server, and the training data 520 may reside in a different second device, such as a local client (e.g., a TPS system). The training data 520 may be compressed, and then transferred to the server via a communication channel.

Because of the volume effect of detectors (the finite size of the detector provides an average response over the sensitive volume), the penumbra of the dose profiles obtained from the simulation may get larger than actual beam characteristics. Simulation data taken from the penumbra of the measured dose profiles, when used to train a DL model, may introduce prediction errors in one or more beam model parameters, such as primary sigma or scatter distance, among other VSM parameters. To avoid or reduce such prediction errors, additive noise may be applied to the simulation data 522 to more realistically represent scanning data in a clinical setting, such that by using such "noisy" training data the deep learning model may be refined. For example, difference between the calculated dose profile and the measured dose profile, referred to as dose noise, can be added to at least a portion of the simulation data 522 to produce "noisy" training data that would represent more realistically actual clinical data. Training the DL model using the noisy training data can improve the robustness of a trained DL model.

The DL training process 508 may include a training data preprocessing 531 operation that pre-process the training data such as to mitigate certain deficiencies of the training data. As described above, noise maybe artificially added to the simulation data before the simulation data are used for DL training process 508. The preprocessing 531 may include a denoising operation (e.g., a computational model) can remove or attenuate noise from the simulation data. In some examples, the denoising operation can be integrated into the DL model. For example, the denoising can be implemented as a fully connected layer in a CNN. The denoising layer in the CNN may be trained separately from the rest of the DL model. The training data of the denoising model can include measured dose profiles and XVMC calculated data of delivered model. In an example of training the denoising model, the measured dose profiles can be fed into the denoising module to generate estimated XVMC calculated dose profiles. The estimated profiles can be compared to the calculated dose, the sum of difference of each dose points are considered as a penalty for optimizing the denoising module. Alternatively, the denoising layer may be trained together with the rest of the DL model. The inclusion of the process of denoising the training data can improve the model parameter predication performance of the trained DL model. In some examples, the training data preprocessing 531 operation may include converting the training data into a desired data format, such as re-arranging sequences of PDD data and/or the dose profile data in the 2D dose matrix, without changing the value of data points for feature recognition.

The preprocessed simulation data can be fed into the DL model 510 to generate estimated results 532, such as values of the beam model parameters (e.g., VSM parameters) to be predicted. The estimated results 532 can be compared to the expected results 524, such as known values X* of those beam model parameters {X} (e.g., VSM model parameters $\{X_{VSM}\}$) that have been used in dose simulation to produce the simulation data 522. At 533, an estimation error can be computed such as a difference between the estimated results 532 and the expected results 524. The estimation error can be compared to model convergence or training stop criteria at 534, such as proceeding to a sustained minimum for a specified number of training iterations. If the convergence or training stop criteria has not been satisfied, the estimation error can be used to update DL model parameters (Θ, e.g., layer node weights and biases), such as through backpropagation, to reduce or minimize errors in the machine parameter or the estimations errors during subsequent training trials. Another batch of training data can then be selected from the training data 520 and expected results for another iteration of DL model training. In an example, model parameter update using the estimation error may be carried out to minimize or reduce a loss function (or objective function, or cost function). An example of the loss function is square estimation error, as given in Equation (1):

$$J(\Theta^*) = \arg\min_\Theta \|Y - Y^*\|^2 \quad (1)$$

where Y can represent the estimated values of the beam model parameters X (the estimated results 532), Y* can represent the known values of the beam model parameters X* (the expected results 524), and where Θ* can represent ideal parameters of the DL model (e.g., layer node weights and biases as described above) that minimize the squared error between Y and Y*. Other loss functions may be used, such as log cosh, mean absolute error (MAE), mean squared error (MSE), weighted MSE, Huber loss (smooth MAE), or quantile loss, among others. The values of DL model parameters (Θ) can be iteratively improved.

After updating the parameters of the DL model, the iteration index can be incremented by one. The iteration index can correspond to the number of times that the parameters of the DL model have been updated. Convergence or training stop criteria can be checked at 534. In an example, the convergence or stop criteria may include a value of the iteration index in comparison to a threshold number of iterations. In an example, the convergence or stop criteria may include an estimation error, such as cumulative loss (e.g., difference between the estimated values of the beam model parameters X and the known values of the beam model parameters X*, computed by the loss function as discussed above) over multiple training trials, in comparison to an error threshold. The error threshold can correspond to an asymptotic minimum of all errors determined. In an example, the error threshold can be represented by an accuracy level, such as a tolerance range, relative to the known values of the beam model parameters X*. The accuracy level can be based on how the parameter affects the calculated dose distribution. By way of example and not limitation, Table 1 shows accuracy levels for various VSM parameters.

If at 534 it is determined that the convergence or stop criteria have been satisfied (e.g., the iteration index exceeding the threshold number of iterations, or the cumulative loss falling below the error threshold), then the training process can be halted. The trained DL model 540 can be saved in the memory 116 of data processing device 112, or in a server. Additionally or alternatively, a report containing information about the trained DL model 540 can be output to a user via the user interface 136.

The trained DL model 540 can be deployed to a DL inference process 512 to predict beam model parameters (e.g., VSM parameters) for test data 542 collected from a target radiotherapy system. The test data 542 may include machine scanning data indicative of a configuration or an operation status of the radiation therapy machine. By applying the test data 542 to the trained DL model 540, predicted results 544 (e.g., values of beam model parameters) may be determined. The TPS system can use a beam model that has the predicted beam model parameter values to create a treatment plan.

In some examples, multiple DL models can be trained for different MLC types (e.g., Agility or MLCi2 collimators, both from Elekta AB of Stockholm, Sweden) and/or at different energy levels (e.g., 4, 6, 10, and 15 MV). The trained DL models can be indexed by the MLC types and energy levels, and archived in a server. During testing, a client (e.g., a TPS system) can request access to the trained DL models in the server, query, and retrieve an appropriate DL model according to the MLC type and/or the energy level. The test data 542 can then be applied to the retrieved DL model to determine values of the beam model. A beam model file can be updated by replacing the default values of the beam model parameters with the parameter values determined by the DL model. The beam model file can then be transferred from the server to the client, where a therapy treatment plan can be generated based on the beam model.

In some examples, the trained DL model 540 can be validated before being tested in the DL inference process 512. Validation data can be generated using a similar approach to the generation of training data 520. In an example, the validation data may include samples randomly taken from the 2D dose matrices corresponding to the dose surface plot 750. The samples included in the validation data may be different from the sampled in the simulation data 522 used for DL training process 508. Applying the validation data to the trained model 540 can yield predicted values of the beam model parameters X. The DL model is deemed to pass the validation check if a difference between the predicted beam model parameter value X and the known beam model parameter value X* falls within a specified accuracy level. Examples of accuracy levels for various parameters of a VSM beam model that a DL model is trained to predict are shown in Table 1.

In some examples, the validation data used for validating the DL model 540 may include measured clinical dose data (as opposed to simulation data obtained from a simulation as discussed above). The clinical dose data, such as PPD and dose profile data collected from multiple sites (e.g., 5-10 sites) with respective field sizes, can be applied to the DL model 540. A batch validation process can predict beam model parameters, and the dose engine can use the beam model with the predicted beam model parameters to calculate dose metrics. If the calculated dose metrics are substantially equivalent to the clinical dose metrics, the DL model is deemed to pass the validation check. The DL model can then be released to the beam modeling process where a beam model can be generated and provided to the TPS to calculate a dose metric and to generate a radiotherapy treatment plan.

TABLE 1

Accuracy levels of VSM parameters

| Parameter Category | Beam Model Parameter | Accuracy Level |
|---|---|---|
| OF | Primary photon | 0.01 |
| | Primary sigma | 0.01 |
| | Scatter distance | 0.1 |
| | Scatter sigma | 0.1 |
| Spectrum | Energy min | 0.05 |
| | Energy max | 0.1 |
| | B-value | 0.05 |
| | Secondary B-value | 0.1 |
| Build-up region | Charged particle | 0.001 |
| | Charged radius | 0.1 |
| | Charged E mean | 0.1 |
| | Charged E max | 0.3 |

Figure 6A:
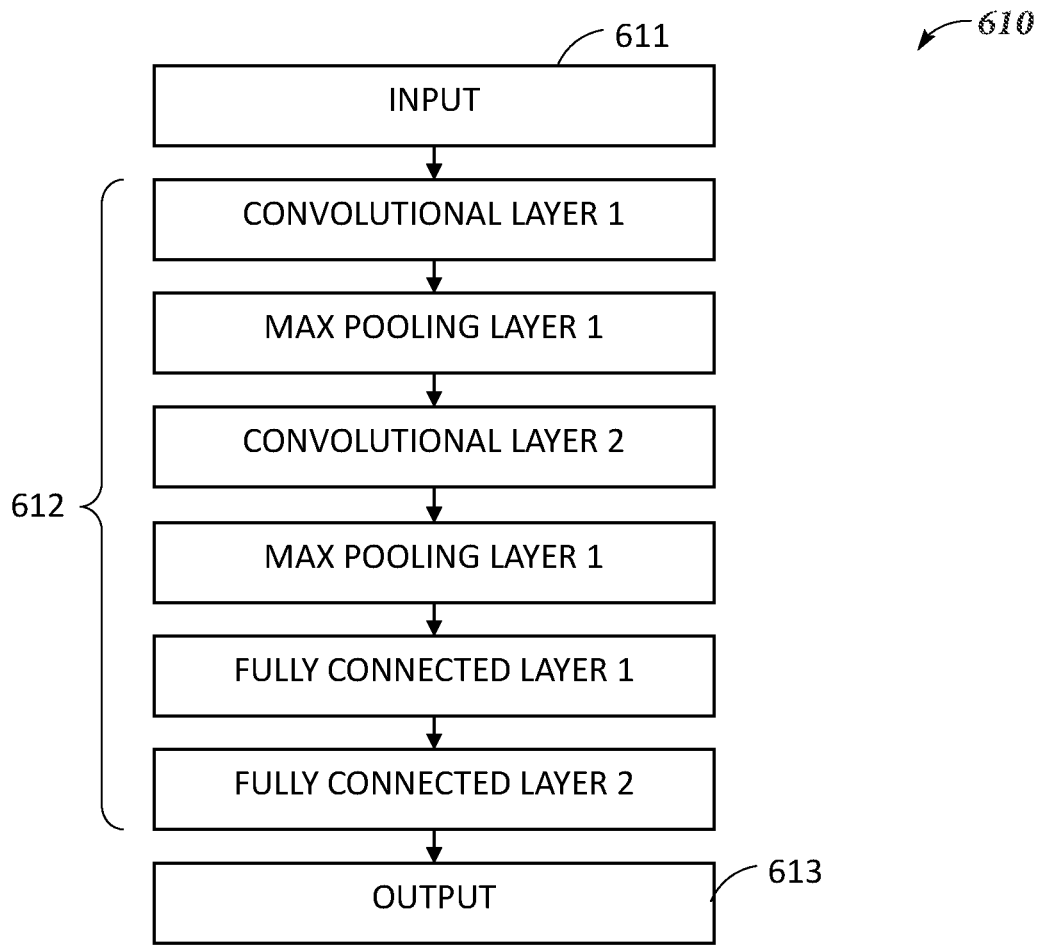
FIG. 6A is a block diagram illustrating an exemplary convoluted neural network (CNN) that may be constructed and trained to predict beam model parameters.
Figure 6B:
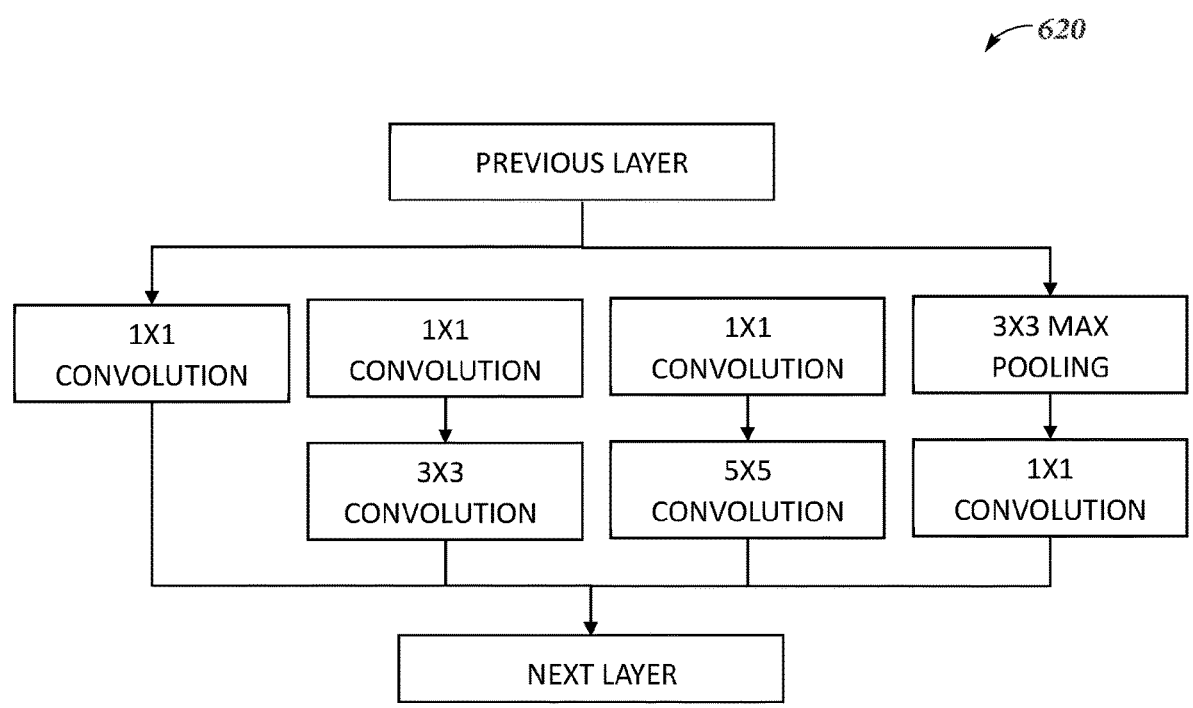
FIG. 6B is a block diagram illustrating an exemplary structure of an Inception Module in a convolutional layer of the CNN in FIG. 6A.

FIGS. 6A and 6B illustrate a convolutional neural network (CNN) to predict VSM parameters. A CNN network can automatically learn the characteristics of data from samples, eliminating the complex feature extraction in conventional machine learning models which generally requires substantial expert knowledge. CNN has been used in analyzing image, especially in recognizing hierarchical patterns in data. Additional advantage of the CNN is that by means of weight sharing, the scale of CNN parameters can be greatly reduced. As a result, the complexity of the training process can be reduced, the converging speed can be increased, and the model generalization ability can be enhanced.

FIG. 6A is a diagram illustrating an exemplary architecture of a LeNet CNN 610. The LeNet CNN 610 include one input layer 611, intermediate learning layers 612, and an output layer 613. In the illustrated example, the intermediate learning layers 612 comprises two convolutional layers, and two fully connected layers. Each convolutional layer is followed by a max-pooling layer. The max-pooling is a form of non-linear down-sampling. Max-pooling partitions the input into a set of non-overlapping sub-regions, and outputs the maximum value for each such sub-region. The max-pooling can help reduce reducing the dimensionality of the intermediate representation, reduce overall computation, and improve robustness of the CNN.

To detect the variation of beam characteristics with several field sizes, the standard convolution layer can be replaced by an Inception Module. The Inception Module are incorporated into CNNs as a way of reducing computational expense. FIG. 6B is a diagram illustrating an exemplary architecture of an Inception Module 620, also referred to as Inception V1 Module, in a convolutional layer of the LeNet CNN 610 in FIG. 6A. The Inception Module 620 may include multiple parallels convolution filters with respective kernel sizes on the same layer. The kernel sizes can be modified based on the individual CNN. As depicted, the Inception Module 620 performs a convolution (e.g., in convolution layer 1) using three different sizes of filters (1×1, 3×3, 5×5). The 1×1 convolution, 3×3 convolution, and 5×5 convolution can be performed on the same level, as illustrated in FIG. 6B. As such, the network gets progressively wider. Max-pooling (e.g., 3×3 max-pooling) can be performed in the inception module. The resulting outputs can be concatenated and sent to the next layer. To make the process even less computationally expensive, an extra 1×1 convolution can be added before each of the 3×3 convolution and 5×5 convolution layers. As such, the number of input channels is limited, and 1xi convolutions are cheaper than 3×3 convolution and 5×5 convolution. The 1xi convolution is added after the 3×3 max-pooling layer. In some examples, variations of the Inception V1 module, such as Inception V2, Inception V3, Inception V4, or Inception-ResNet, may be used to replace the convolution layers in the LeNet 610.

Figure 8:
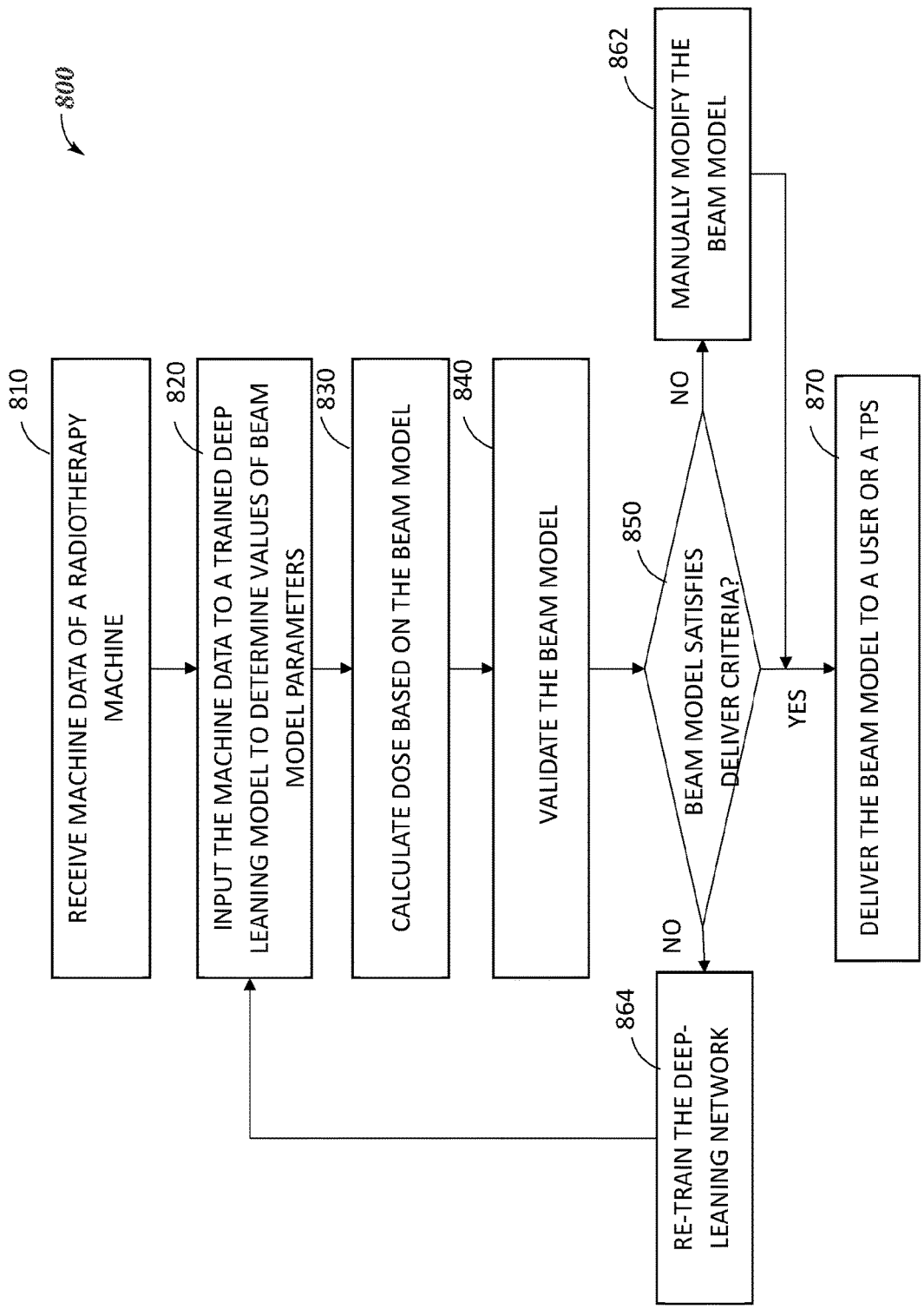
FIG. 8 is a flow chart illustrating an exemplary method of an AI-based modeling and validation of a beam model for use in radiotherapy treatment planning.

FIG. 8 is a flow chart illustrating an exemplary method 800 of AI-based modeling and validation of a beam model for use in radiotherapy treatment planning. The method 800 can predict parameter values for a beam model, such as a virtual source model (VSM), using a trained deep learning (DL) model. In an example, the method 800 may be implemented in and executed by the radiotherapy system 100, which may include a radiation therapy machine to provide radiotherapy to a subject according to a treatment plan.

At 810, machine scanning data can be received or otherwise measured from a radiation therapy machine. The machine scanning data may include information about settings of the radiation therapy machine, dose distributions and dose profiles under different testing conditions. In an example, the machine scanning data represent beam characteristics of a linac head, and can be measured by one or more radiation detectors (e.g., an ion chamber) in a water phantom. Examples of the scanning data may include a percentage depth dose (PDD) that characterizes relative dose quantity determined as the ratio between the axis dose at a specific depth (z, such as within a range of 0-300 mm) and the axis dose at a reference dose depth ($z_0$), and a dose profile that characterizes off-axis dose distribution, such as doses at diagonals, or a percentile radial dose (PRD) profile representing changes of relative dose with a radial distance.

At 820, the received machine scanning data can be applied to a trained deep-leaning (DL) model to determine values of beam model parameters for a beam model including, for example, a size and position of one or more photon sources within the radiation therapy machine, a maximum energy of a photon spectrum for photons emitted from the radiation therapy machine, a number of factors describing the shape of a photon spectrum emitted from the radiation therapy machine, a size and position of one or more electron sources within the radiation therapy machine, an average energy of an electron spectrum emitted from the radiation therapy machine, or one or more numbers describing how radiation (e.g., electrons or photons) emitted by the radiation therapy machine can vary off-axis, among others. The DL model can be pre-trained, such as using the training module 151. As discussed above, training of the DL model can be carried out using the exemplary process 500. Examples of the DL model may include a convolutional neural network. (CNN), a recurrent neural network. (RNN), a long-term and short-term memory (LSTM) network, a deep belief network (DBN), a generative adversarial network, a machine learning model, a transfer learning module, a hybrid neural network comprising two or more neural network models of different types or different model configurations, or any type of artificial intelligence based model. The architectures and parameters of the DL model can vary depending on the beam model to be predicted. In an example, the beam model is a VSM model as depicted in FIG. 4. Exemplary CNN models for predicting model parameter values for a VSM are described above with reference to FIGS. 6A-6B. In some examples, the trained DL model may include a trained denoising module (e.g., a computational model) to pre-process the received machine scanning data. The pre-processing module may be implemented as a fully connected layer in a denoising module of CNN, and trained to remove or attenuate noise from the received machine scanning data. The denoising module can be trained separately from the rest of the DL model. The inclusion of a pre-processing module in the DL model can improve the robustness of prediction of beam model parameters. The pre-processed data may be converted to a desired data format before being used for prediction of values of beam model parameters. For example, sequences of PDD data and/or the dose profile data in a 2D dose matrix as described above with reference to FIG. 7E may be re-arranged without changing the value of data points for feature recognition.

At 830, dose metric can be calculated in a virtual phantom (e.g., a water phantom) using the beam model that has the predicted model parameter values obtained from the trained DL model from 820, such as using the dose engine. Examples of the dose engine may include a voxel Monte Carlo (VMC) dose engine, or an X-ray voxel Monte Carlo (XVMC) dose engine. Various algorithms may be used to calculate the dose, including, for example, a Monte Carlo dose algorithm, such as an XVMC algorithm. In an example, the beam model can be imported into a TPS (e.g., Monaco® treatment planning system, manufactured by Elekta AB of Stockholm, Sweden), which can calculate the dose distribution in a virtual phantom using a Monte Carlo algorithm (implemented as a software package stored in the software programs 144).

At 840, the beam model having the model parameters determined based on the DL models can be validated before being deployed for clinical treatment planning. The calculated dose from step 830 can be compared with the measurements to determine if the calculated dose satisfies dosimetric verification criteria, also referred to as delivery criteria, such as one or more dose metrics falling within a tolerance range (±x %) with respect to the measured dose metrics. Examples of the delivery criteria may include any of: central ray within ±2% tolerance, high does at low gradient within a 3% tolerance, high gradient (e.g., 30%/cm) within a 3% tolerance at 3 mm, low dose at low gradient within a 3% tolerance, output factors within a 2% tolerance. In some examples, the delivery criteria may include manual inspection and validation. For example, a modeling physicist can grade the beam model (e.g., the VSM model), such as in a user interface, as one of "Pass" (indicating the model is ready to delivered), "Fail" (indicating the model is unacceptable for delivery), or "Improvement Needed" (indicating further tuning of beam model parameter is needed). The modeling physicist may further add annotations to indicate various characteristics of dose that need to improved, such as spectrum, output factors (OF, at the reference depth), buildup region (the range of depth for the attenuation of electron contamination) of PDDs, horn (an increase in beam intensity away from the central axis, dependent mostly on flattening filter design) and penumbra (around the geometric beam edge) of profiles, among others.

If at 850, the beam model satisfies the delivery criteria, then the beam model can be output to a user, or deployed to a TPS for clinical treatment planning at 870. The TPS can generate a radiation therapy treatment plan using the beam model, the medical images (e.g., imaging data associated with a patient anatomical region, organ, or volume of interest segmentation data), and patient data (e.g., functional organ modeling data, radiation dosage data (e.g., DVH information), and other clinical information about the patient and treatment).

If at 850, the beam model does not satisfy the delivery criteria, then the beam model can be modified at 862, such as by a human modeler (e.g., a modeling physicist) that manually tune one or more beam model parameters until it is ready to be deployed to the TPS. Alternatively, in the event of a failed beam model the DL model, the DL model can be retrained or adjusted at 864, and then used to predict a new set of beam model parameters. A beam model that has the new set of model parameters can be validated at 840.

Figure 9:
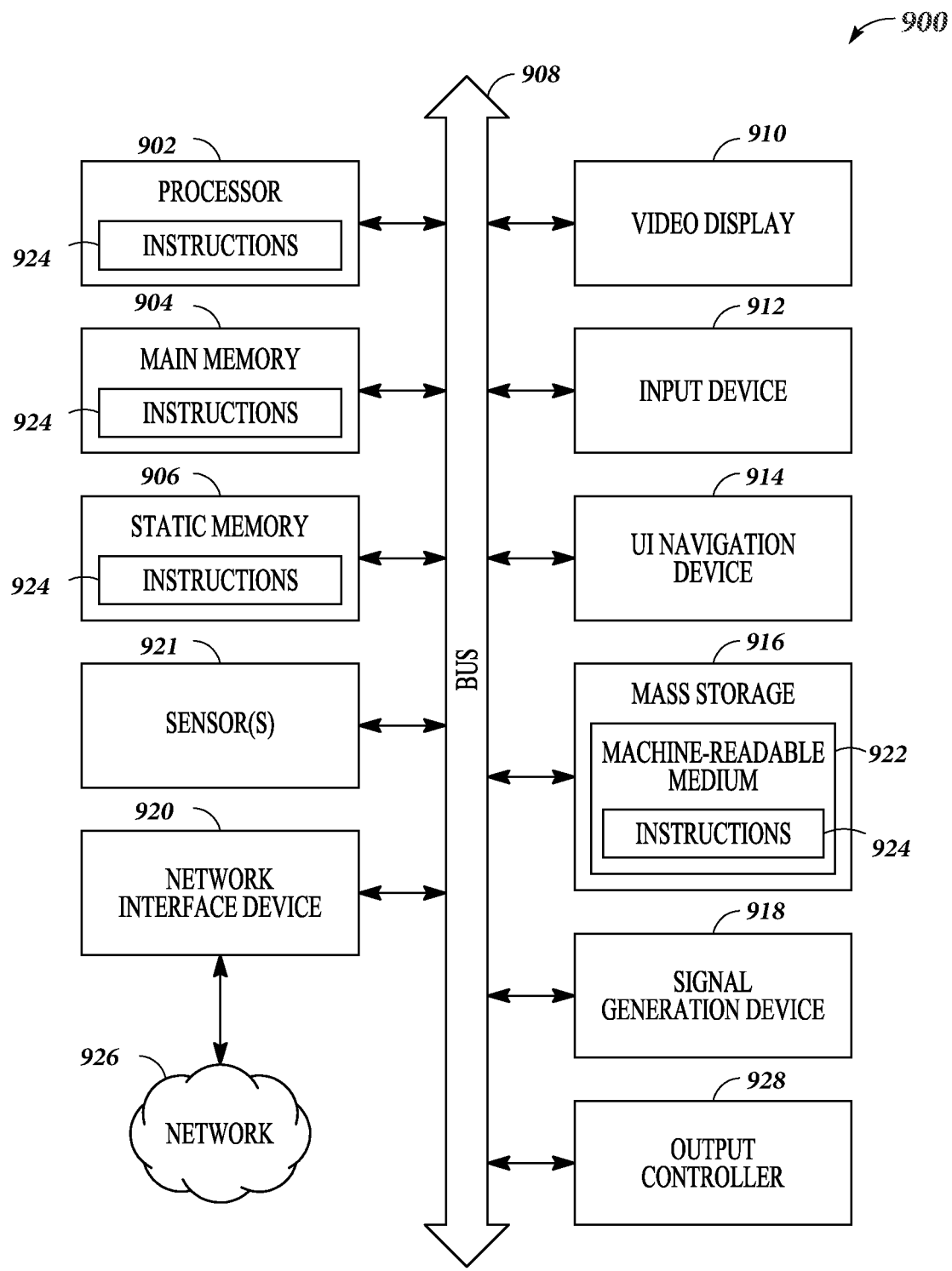
FIG. 9 illustrates generally a block diagram of an example machine upon which any one or more of the techniques (e.g., methodologies) discussed herein may perform.

FIG. 9 illustrates a block diagram of an example of a machine 900 on which one or more of the methods as discussed herein can be implemented. In one or more examples, one or more items of the data processing device 112 can be implemented by the machine 900. In alternative examples, the machine 900 operates as a standalone device or may be connected (e.g., networked) to other machines. In one or more examples, the data processing device 112 may include one or more of the items of the machine 900. In a networked deployment, the machine 900 may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example machine 900 includes a processor 902 (e.g., a central processing unit (CPU), a graphics processing unit (GPU), an application specific integrated circuit, circuitry, such as one or more transistors, resistors, capacitors, inductors, diodes, logic gates, multiplexers, buffers, modulators, demodulators, radios (e.g., transmit or receive radios or transceivers), sensors 921 (e.g., a transducer that converts one form of energy (e.g., light, heat, electrical, mechanical, or other energy) to another form of energy), or the like, or a combination thereof), a main memory 904 and a static memory 906, which communicate with each other via a bus 908. The machine 900 (e.g., computer system) may further include a video display unit 910 (e.g., a liquid crystal display (LCD) or a cathode ray tube (CRT)). The machine 900 also includes an alphanumeric input device 912 (e.g., a keyboard), a user interface (UI) navigation device 914 (e.g., a mouse), a disk drive or mass storage unit 916, a signal generation device 918 (e.g., a speaker) and a network interface device 920.

The disk drive unit 916 includes a machine-readable medium 922 on which is stored one or more sets of instructions and data structures (e.g., software) 924 embodying or utilized by any one or more of the methodologies or functions described herein. The instructions 924 may also reside, completely or at least partially, within the main memory 904 and/or within the processor 902 during execution thereof by the machine 900, the main memory 904 and the processor 902 also constituting machine-readable media.

The machine 900 as illustrated includes an output controller 928. The output controller 928 manages data flow to/from the machine 900. The output controller 928 is sometimes called a device controller, with software that directly interacts with the output controller 928 being called a device driver.

While the machine-readable medium 922 is shown in an example to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present invention, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; and CD-ROM and DVD-ROM disks.

The instructions 924 may further be transmitted or received over a communications network 926 using a transmission medium. The instructions 924 may be transmitted using the network interface device 920 and any one of a number of well-known transfer protocols (e.g., HTTP). Examples of communication networks include a local area network ("LAN"), a wide area network ("WAN"), the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

As used herein, "communicatively coupled between" means that the entities on either of the coupling must communicate through an item therebetween and that those entities cannot communicate with each other without communicating through the item.

Below are provided further descriptions of various non-limiting, exemplary embodiments. The below-described exemplary embodiments may be practiced in conjunction with one or more other aspects or exemplary embodiments. That is, the exemplary embodiments of the invention, such as those described below, may be implemented, practiced, or utilized in any combination (for example, any combination that is suitable, practicable, and/or feasible) and are not limited only to those combinations described herein and/or included in the appended claims.

Example 1 is a system for generating a beam model for a radiation therapy treatment plan used to treat a patient via a radiation therapy device. The system comprises: a memory to store a trained deep learning (DL) model and a plurality of beam model parameters; and a processor circuit configured to: receive machine scanning data indicative of a configuration or an operation status of a radiation therapy device; apply the received machine scanning data to the trained DL model to determine values for the plurality of beam model parameters; generate a beam model based on the determined values of the plurality of beam model parameters; and store the beam model in the memory accessible by a user or a treatment planning system.

In Example 2, the subject matter of Example 1 optionally includes the beam model that may include one or more virtual particle sources including: a primary photon source; a scatter photon source; or an electron contamination source.

In Example 3, the subject matter of any one or more of Examples 1-2 optionally includes the processor circuit that may include a training module configured to: access simulated machine scanning data measured in a radiation simulation, wherein the simulated machine scanning data is measured by the radiation therapy device programmed with known values of beam model parameters; construct a set of training data based on the simulated machine scanning data; and train a DL model by applying the set of training data and the known values of the beam model parameters.

In Example 4, the subject matter of Example 3 optionally includes the simulated machine scanning data that may include at least one dose characteristic including: a percentage depth dose (PDD) curve; a dose profile; a dose-volume histogram; an overlap volume histogram; or a three-dimensional dose distribution.

In Example 5, the subject matter of any one or more of Examples 3-4 optionally includes the simulated machine scanning data that may include a plurality of dose profiles corresponding to a plurality of field sizes, and the training module is configured to: interpolate dose values between at least two of the plurality of dose profiles corresponding to different field sizes; and construct the set of training data using samples taken from the plurality of dose profiles including the interpolated dose values.

In Example 6, the subject matter of Example 5 optionally includes the training module that may be configured to: generate a two-dimensional (2D) dose matrix using the plurality of dose profiles corresponding to a plurality of field sizes, the 2D dose matrix representing dose values for a plurality of positions and corresponding to the plurality of field sizes; and construct the set of training data by sampling the 2D dose matrix at a sampling resolution according to field size.

In Example 7, the subject matter of any one or more of Examples 3-6 optionally includes the training module that may be configured to apply additive noise to the simulated machine scanning data to construct the set of training data that allows the DL model to be refined.

In Example 8, the subject matter of any one or more of Examples 3-7 optionally includes a first device including the training module, and a second device configured to receive the trained DL model from the first device via a communication channel, and to generate the beam model by applying the received machine scanning data to the DL model.

In Example 9, the subject matter of any one or more of Examples 1-8 optionally includes the trained DL model that may include at least one of: a convolutional neural network (CNN); a recurrent neural network (RNN); a long-term and short-term memory (LSTM) network; a deep belief network (DBN); a generative adversarial network; a machine learning model; a transfer learning module; or an artificial intelligence-based learning model.

In Example 10, the subject matter of Example 9 optionally includes the trained DL model that may include a CNN with an inception module.

In Example 11, the subject matter of any one or more of Examples 1-10 optionally includes the trained DL model that may include a denoising module, and the processor circuit is configured to generate the trained DL model including to train the denoising module to remove or attenuate noise from the training data.

In Example 12, the subject matter of any one or more of Examples 1-11 optionally includes the processor circuit that may further be configured to: calculate a dose profile using the generated beam model with the determined values of the beam model parameters; and determine that the beam model passes a validation check if the calculated dose profile satisfies a condition relative to beam characteristics measured from the radiation therapy device.

In Example 13, the subject matter of any one or more of Examples 1-12 optionally includes the treatment planning system configured to generate a radiation therapy treatment plan for the patient based on the beam model.

In Example 14, the subject matter of any one or more of Examples 1-13 optionally includes a user interface configured to present the trained DL model or the beam model to the user.

Example 15 is a method for generating a beam model for a radiation therapy treatment plan used to treat a patient via a radiation therapy device, the method comprising: receiving machine scanning data indicative of a configuration or an operation status of the radiation therapy device; providing a trained deep learning (DL) model associated with a plurality of beam model parameters; applying the received machine scanning data to the trained DL model to determine values for the plurality of beam model parameters; generating a beam model based on the determined values of the plurality of beam model parameters; and outputting the beam model to a user or a treatment planning system.

In Example 16, the subject matter of Example 15 optionally includes the beam model that may include one or more virtual particle sources including: a primary photon source; a scatter photon source; or an electron contamination source.

In Example 17, the subject matter of any one or more of Examples 15-16 optionally includes: accessing simulated machine scanning data measured in a radiation simulation, wherein the simulated machine scanning data is measured by the radiation therapy device programmed with known values of beam model parameters; constructing a set of training data based on the simulated machine scanning data; and generating the trained DL model by applying the set of training data and the known values of the beam model parameters.

In Example 18, the subject matter of Example 17 optionally includes the simulated machine scanning data that may include a plurality of dose profiles corresponding to a plurality of field sizes, and wherein constructing the set of training data includes: interpolating dose values between at least two of the plurality of dose profiles corresponding to different field sizes; and constructing the set of training data using samples taken from the plurality of dose profiles including the interpolated dose values.

In Example 19, the subject matter of Example 18 optionally includes constructing the set of training data that may include: generating a two-dimensional (2D) dose matrix using the plurality of dose profiles corresponding to a plurality of field sizes, the 2D dose matrix representing dose values for a plurality of positions and corresponding to the plurality of field sizes; and sampling the 2D dose matrix at a sampling resolution according to field size.

In Example 20, the subject matter of any one or more of Examples 18-19 optionally includes applying additive noise to the simulated machine scanning data to construct the set of training data that allows the DL model to be refined.

In Example 21, the subject matter of any one or more of Examples 15-20 optionally includes the trained DL model that may include a convolutional neural network (CNN) with an inception module.

In Example 22, the subject matter of any one or more of Examples 15-21 optionally includes the trained DL model that may include a denoising module, and generating the trained DL model that may include training the denoising module to remove or attenuate noise from the set of training data.

In Example 23, the subject matter of any one or more of Examples 15-22 optionally includes: calculating a dose profile using the generated beam model with the determined values of the beam model parameters; and determining that the beam model passes a validation check if the calculated dose profile satisfies a condition relative to beam characteristics measured from the radiation therapy device.

In Example 24, the subject matter of any one or more of Examples 15-23 optionally includes generating, via the treatment planning system, a radiation therapy treatment plan for the patient based on the beam model.

Additional Notes

The above detailed description includes references to the accompanying drawings, which form a part of the detailed description. The drawings show, by way of illustration but not by way of limitation, specific examples in which the disclosure can be practiced. These examples are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the disclosure or in the examples thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended aspects, the terms "including" and "in which" are used as the plain-English equivalents of the respective terms "comprising" and "wherein." Also, in the following aspects, the terms "comprising," "including," and "having" are intended to be open-ended to mean that there may be additional elements other than the listed elements, such that after such a term (e.g., comprising, including, having) in a aspect are still deemed to fall within the scope of that aspect. Moreover, in the following aspects, the terms "first," "second," and "third," and so forth, are used merely as labels, and are not intended to impose numerical requirements on their objects.

Examples of the disclosure may be implemented with computer-executable instructions. The computer-executable instructions (e.g., software code) may be organized into one or more computer-executable components or modules. Aspects of the disclosure may be implemented with any number and organization of such components or modules. For example, aspects of the disclosure are not limited to the specific computer-executable instructions or the specific components or modules illustrated in the figures and described herein. Other examples of the disclosure may include different computer-executable instructions or components having more or less functionality than illustrated and described herein.

Method examples (e.g., operations and functions) described herein can be machine or computer-implemented at least in part (e.g., implemented as software code or instructions). Some examples may include a computer-readable medium or machine-readable medium encoded with instructions operable to configure an electronic device to perform methods as described in the above examples. An implementation of such methods may include software code, such as microcode, assembly language code, a higher-level language code, or the like (e.g., "source code"). Such software code may include computer readable instructions for performing various methods (e.g., "object" or "executable code"). The software code may form portions of computer program products. Software implementations of the examples described herein may be provided via an article of manufacture with the code or instructions stored thereon, or via a method of operating a communication interface to send data via a communication interface (e.g., wirelessly, over the internet, via satellite communications, and the like).

Further, the software code may be tangibly stored on one or more volatile or non-volatile computer-readable storage media during execution or at other times. These computer-readable storage media may include any mechanism that stores information in a form accessible by a machine (e.g., computing device, electronic system, and the like), such as, but are not limited to, floppy disks, hard disks, removable magnetic disks, any form of magnetic disk storage media, CD-ROMS, magnetic-optical disks, removable optical disks (e.g., compact disks and digital video disks), flash memory devices, magnetic cassettes, memory cards or sticks (e.g., secure digital cards), RAMs (e.g., CMOS RAM and the like), recordable/non-recordable media (e.g., read only memories (ROMs)), EPROMS, EEPROMS, or any type of media suitable for storing electronic instructions, and the like. Such computer readable storage medium coupled to a computer system bus to be accessible by the processor and other parts of the OIS.

In an example, the computer-readable storage medium may have encoded a data structure for a treatment planning, wherein the treatment plan may be adaptive. The data structure for the computer-readable storage medium may be at least one of a Digital Imaging and Communications in Medicine (DICOM) format, an extended DICOM format, a XML format, and the like. DICOM is an international communications standard that defines the format used to transfer medical image-related data between various types of medical equipment. DICOM RT refers to the communication standards that are specific to radiation therapy.

In various examples of the disclosure, the method of creating a component or module can be implemented in software, hardware, or a combination thereof. The methods provided by various examples of the present disclosure, for example, can be implemented in software by using standard programming languages such as, for example, C, C++, Java, Python, and the like; and combinations thereof. As used herein, the terms "software" and "firmware" are interchangeable, and include any computer program stored in memory for execution by a computer.

A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a system for performing the operations herein. This system may be specially constructed for the required purposes, or it may comprise a general purpose computer selectively activated or reconfigured by a computer program stored in the computer. The order of execution or performance of the operations in examples of the disclosure illustrated and described herein is not essential, unless otherwise specified. That is, the operations may be performed in any order, unless otherwise specified, and examples of the disclosure may include additional or fewer operations than those disclosed herein. For example, it is contemplated that executing or performing a particular operation before, contemporaneously with, or after another operation is within the scope of aspects of the disclosure.

In view of the above, it will be seen that the several objects of the disclosure are achieved and other advantageous results attained. Having described aspects of the disclosure in detail, it will be apparent that modifications and variations are possible without departing from the scope of aspects of the disclosure as defined in the appended aspects. As various changes could be made in the above constructions, products, and methods without departing from the scope of aspects of the disclosure, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the disclosure without departing from its scope. While the dimensions, types of materials and coatings described herein are intended to define the parameters of the disclosure, they are by no means limiting and are exemplary examples. Many other examples will be apparent to those of skill in the art upon reviewing the above description. The scope of the disclosure should, therefore, be determined with reference to the appended aspects, along with the full scope of equivalents to which such aspects are entitled.

Also, in the above Detailed Description, various features may be grouped together to streamline the disclosure. This should not be interpreted as intending that an unexpected disclosed feature is essential to any aspect. Rather, inventive subject matter may lie in less than all features of a particular disclosed example. Thus, the following aspects are hereby incorporated into the Detailed Description, with each aspect standing on its own as a separate example. The scope of the disclosure should be determined with reference to the appended aspects, along with the full scope of equivalents to which such aspects are entitled. Further, the limitations of the following aspects are not written in means-plus-function format and are not intended to be interpreted based on 35 U.S.C. § 112, sixth paragraph, unless and until such aspect limitations expressly use the phrase "means for" followed by a statement of function void of further structure.

The Abstract is provided to allow the reader to quickly ascertain the nature of the technical disclosure. It is submitted with the understanding that it will not be used to interpret or limit the scope or meaning of the aspects.

What is claimed is:

1. A system for generating a beam model for a radiation therapy treatment plan used to treat a patient via a radiation therapy device, the system comprising:
   a training module configured to:
      access simulated machine scanning data measured in a radiation simulation by the radiation therapy device programmed with known values of a plurality of beam model parameters;
      interpolate or extrapolate the simulated machine scanning data at a finer resolution of depth or a finer resolution of field size;
      construct a set of training data comprising data samples taken from the simulated machine scanning data and the interpolated or extrapolated simulated machine scanning data; and
      train a deep learning model using the set of training data and the known values of the plurality of beam model parameters;
   a memory to store the trained deep learning model and the plurality of beam model parameters; and
   a processor circuit configured to:
      receive machine scanning data indicative of a configuration or an operation status of the radiation therapy device;
      apply the received machine scanning data to the trained deep learning model to determine values for the plurality of beam model parameters;
      generate a beam model based on the determined values of the plurality of beam model parameters; and
      store the beam model in the memory accessible by a user or a treatment planning system.

2. The system of claim 1, wherein the beam model includes one or more virtual particle sources including:
   a primary photon source;
   a scatter photon source; or
   an electron contamination source.

3. The system of claim 1, wherein the simulated machine scanning data includes at least one dose characteristic including:
   a percentage depth dose (PDD) curve;
   a dose profile;
   a dose-volume histogram;
   an overlap volume histogram; or
   a three-dimensional dose distribution.

4. The system of claim 1, wherein the simulated machine scanning data includes a plurality of dose profiles corresponding to a plurality of field sizes,
   wherein to interpolate or extrapolate the simulated machine scanning data includes to interpolate or extrapolate dose values between at least two of the plurality of dose profiles corresponding to different field sizes,
   wherein the training data includes using samples taken from the plurality of dose profiles including the interpolated or extrapolated dose values.

5. The system of claim 4, wherein the training module is configured to:
   generate a two-dimensional (2D) dose matrix using the plurality of dose profiles corresponding to a plurality of field sizes, the 2D dose matrix representing dose values calculated for a plurality of positions and a plurality of field sizes; and
   construct the set of training data by sampling the 2D dose matrix at a sampling resolution according to field size.

6. The system of claim 1, wherein the training module is configured to apply additive noise to the simulated machine scanning data to construct the set of training data that allows the deep learning model to be refined.

7. The system of claim 1, comprising:
   a first device including the training module; and
   a second device configured to receive the trained deep learning model from the first device via a communication channel, and to generate the beam model by applying the received machine scanning data to the deep learning model.

8. The system of claim 1, wherein the trained deep learning model includes at least one of:
   a convolutional neural network (CNN);
   a recurrent neural network (RNN);
   a long-term and short-term memory (LSTM) network;
   a deep belief network (DBN);
   a generative adversarial network;
   a machine learning model;
   a transfer learning module; or
   an artificial intelligence-based learning model.

9. The system of claim 8, wherein the trained deep learning model includes a CNN with an inception module.

10. The system of claim 1, wherein the trained deep learning model includes a denoising module, and the processor circuit is configured to generate the trained deep learning model including to train the denoising module to remove or attenuate noise from the training data.

11. The system of claim 1, wherein the processor circuit is further configured to:
   calculate a dose profile using the generated beam model with the determined values of the plurality of beam model parameters; and
   determine that the beam model passes a validation check if the calculated dose profile satisfies a condition relative to beam characteristics measured from the radiation therapy device.

12. The system of claim 1, comprising the treatment planning system configured to generate a radiation therapy treatment plan for the patient based on the beam model.

13. The system of claim 1, comprising a user interface configured to present the trained deep learning model or the beam model to the user.

14. A method for generating a beam model for a radiation therapy treatment plan used to treat a patient via a radiation therapy device, the method comprising:

receiving machine scanning data indicative of a configuration or an operation status of the radiation therapy device;

generating a trained deep learning model, including:
- interpolating or extrapolating simulated machine scanning data at a finer resolution of depth or a finer resolution of field size, the simulated machine scanning data being measured in a radiation simulation by the radiation therapy device programmed with known values of a plurality of beam model parameters;
- constructing a set of training data comprising data samples taken from the simulated machine scanning data and the interpolated or extrapolated simulated machine scanning data; and
- generating the trained deep learning model using the set of training data and the known values of the plurality of beam model parameters;

applying the received machine scanning data to the trained deep learning model to determine values for the plurality of beam model parameters;

generating a beam model based on the determined values of the plurality of beam model parameters; and outputting the beam model to a user or a treatment planning system.

15. The method of claim 14, wherein the beam model includes one or more virtual particle sources including:
- a primary photon source;
- a scatter photon source; or
- an electron contamination source.

16. The method of claim 14, wherein the simulated machine scanning data includes a plurality of dose profiles corresponding to a plurality of field sizes,
wherein interpolating or extrapolating the simulated machine scanning data includes interpolating or extrapolating dose values between at least two of the plurality of dose profiles corresponding to different field sizes,
wherein the training data includes samples taken from the plurality of dose profiles including the interpolated or extrapolated dose values.

17. The method of claim 16, wherein constructing the set of training data includes:
generating a two-dimensional (2D) dose matrix using the plurality of dose profiles corresponding to a plurality of field sizes, the 2D dose matrix representing dose values calculated for a plurality of positions and a plurality of field sizes; and
sampling the 2D dose matrix at a sampling resolution according to field size.

18. The method of claim 16, further comprising applying additive noise to the simulated machine scanning data to construct the set of training data that allows the deep learning model to be refined.

19. The method of claim 14, wherein the trained deep learning model includes a convolutional neural network (CNN) with an inception module.

20. The method of claim 14, wherein the trained deep learning model includes a denoising module, and generating the trained deep learning model includes training the denoising module to remove or attenuate noise from the set of training data.

21. The method of claim 14, further comprising:
calculating a dose profile using the generated beam model with the determined values of the plurality of beam model parameters; and
determining that the beam model passes a validation check if the calculated dose profile satisfies a condition relative to beam characteristics measured from the radiation therapy device.

22. The method of claim 14, comprising generating, via the treatment planning system, a radiation therapy treatment plan for the patient based on the beam model.

* * * * *